United States Patent
Ono et al.

(10) Patent No.: US 8,288,613 B2
(45) Date of Patent: Oct. 16, 2012

(54) LIGNAN HYDROXYLASE

(75) Inventors: Eiichiro Ono, Osaka (JP); Asako Okada, Osaka (JP); Yuko Fukui, Osaka (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 12/745,292

(22) PCT Filed: Dec. 17, 2008

(86) PCT No.: PCT/JP2008/072943
§ 371 (c)(1),
(2), (4) Date: Sep. 3, 2010

(87) PCT Pub. No.: WO2009/084439
PCT Pub. Date: Jul. 9, 2009

(65) Prior Publication Data
US 2011/0104360 A1    May 5, 2011

(30) Foreign Application Priority Data
Dec. 28, 2007  (JP) ................................ 2007-339510

(51) Int. Cl.
*C12N 15/82* (2006.01)
*C12N 15/52* (2006.01)
*C12N 15/63* (2006.01)
*C12N 9/00* (2006.01)
*C12N 15/29* (2006.01)
*C12P 19/04* (2006.01)
*C12P 21/02* (2006.01)

(52) U.S. Cl. ........ 800/284; 800/295; 800/285; 800/323; 536/23.2; 536/23.6; 435/69.1; 435/252.3; 435/468; 435/419; 435/320.1; 435/101; 530/370

(58) Field of Classification Search ........................ None
See application file for complete search history.

(56) References Cited

U.S. PATENT DOCUMENTS

| | | | | |
|---|---|---|---|---|
| 6,121,512 A * | 9/2000 | Siminszky et al. | ............ | 800/298 |
| 6,781,031 B2 * | 8/2004 | Langham | ...................... | 800/260 |
| 2007/0039067 A1 * | 2/2007 | Feldmann et al. | ............ | 800/278 |
| 2007/0271624 A1 | 11/2007 | Ono et al. | | |
| 2008/0293099 A1 | 11/2008 | Ono et al. | | |
| 2009/0241226 A1 | 9/2009 | Ono | | |

FOREIGN PATENT DOCUMENTS

| | | |
|---|---|---|
| JP | 2006/129728 | 5/2006 |
| WO | 2005/030944 A1 | 4/2005 |
| WO | 2006/049315 A1 | 5/2006 |
| WO | 2007/119639 A1 | 10/2007 |

OTHER PUBLICATIONS

Baulcombe (Nature, vol. 431, 2004 pp. 356-363).*
Guo et al, PNAS 2004 (101)25,9205-9210.*
Lehner et al. (Brief. Functional Genomics, 3: 68-83.*
Webb et al (Journal of Plant Physiology, 165 (2008) 1736-1744).*
Lorenc-Kukula (Physiological and Molecular Plant Pathology 70 (2007) 38-48).*
Shimada et al (FEBS Letters 461 (1999) 241-245).*
Abe et al., "9α-Hydroxypinoresinol, 9α-Hydroxymedioresinol and Related Lignans from *Allamanda neriifolia*" *Phytochemistry* vol. 27, No. 2, p. 575-577, 1988.
Davin et al., "Dirigent Proteins and Dirigent Sites Explain the Mystery of Specificity of Radical Precursor Coupling in Lignan and Lignin Biosynthesis" *Plant Physiology*, vol. 123, pp. 453-461, 2000.
Ahmad et al., "Butyrylcholinesterase Inhibitory Lignans from *Sacrostemma viminale*" *Proc. Pakistan Acad. Sci.*, vol. 42, No. 3, pp. 167-171, 2005.
Cho et al., "(+)-Larreatricin Hydroxylase, an Enantio-Specific Polyphenol Oxidase from the Creosote Bush (*Larrea tridentate*)" *PNAS*, vol. 100, No. 19, pp. 10641-10646, 2003.
Turnbull et al., "Mechanistic Studies on Three 2-Oxoglutarate-dependent Oxygenases of Flavonoid Biosynthesis" *The Journal of Biological Chemistry*, vol. 279, No. 2, pp. 1206-1216, 2004.
International Search Report for PCT/JP2008/072943, mailed Mar. 31, 2009.
International Preliminary Report on Patentability for PCT/JP2008/072943, issued Aug. 10, 2010.
Cui et al. "Protective action of 9-hydroxypinoresinol against oxidative damage in brain of mice challenged with kainic acid" *Journal of Pharmacy and Pharmacology* 59:521-22, 2007.
Office Action issued with respect to Chinese Patent Application No. 200810185269.6, dated Jul. 1, 2011 along with a partial English-language translation.
Toshiaki Umezawa, "Diversity in Lignan Biosynthesis" *Phytochemistry Reviews* 2:371-390, 2003.

* cited by examiner

*Primary Examiner* — David T Fox
*Assistant Examiner* — Lee A Visone
(74) *Attorney, Agent, or Firm* — Greenblum & Bernstein, P.L.C.

(57) ABSTRACT

The invention provides an enzyme having a lignan-hydroxylating activity, particularly an enzyme capable of catalyzing the reaction of transferring a hydroxyl group to a lignan, an enzyme capable of catalyzing the hydroxylation of piperitol to 9-hydroxylpiperitol or pinoresinol to 9-hydroxylpinoresinol. The invention provides a polypeptide having a lignan-hydroxylating activity; a polynucleotide encoding the same; a vector or transformant comprising the polynucleotide; a method for producing a polypeptide having a lignan-hydroxylating activity which comprises using the transformant; and so on. The transformant wherein the polynucleotide is expressibly introduced is useful for the hydroxylation of a lignan or for the production of a product using the same in the food sector and a variety of industry sectors.

26 Claims, 5 Drawing Sheets

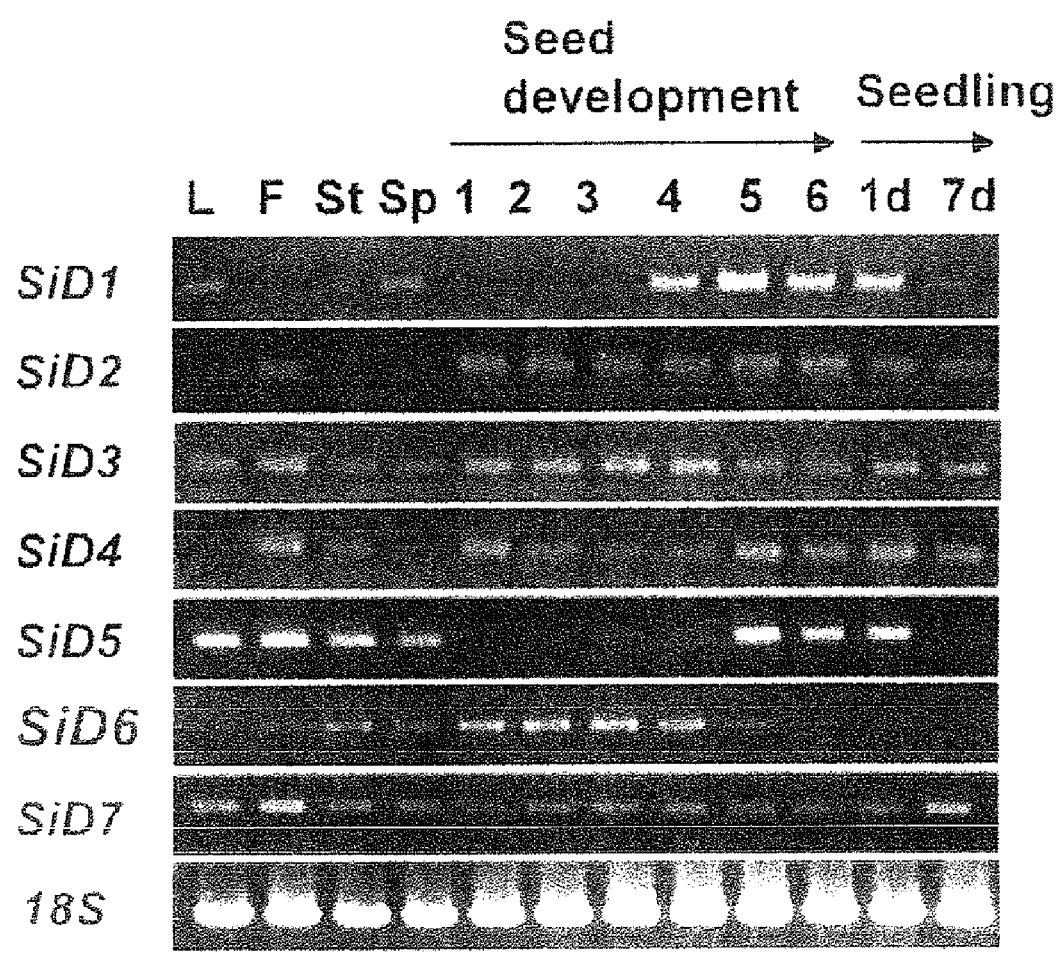
FIG. 1 Expression analysis of SiD genes by RT-PCR

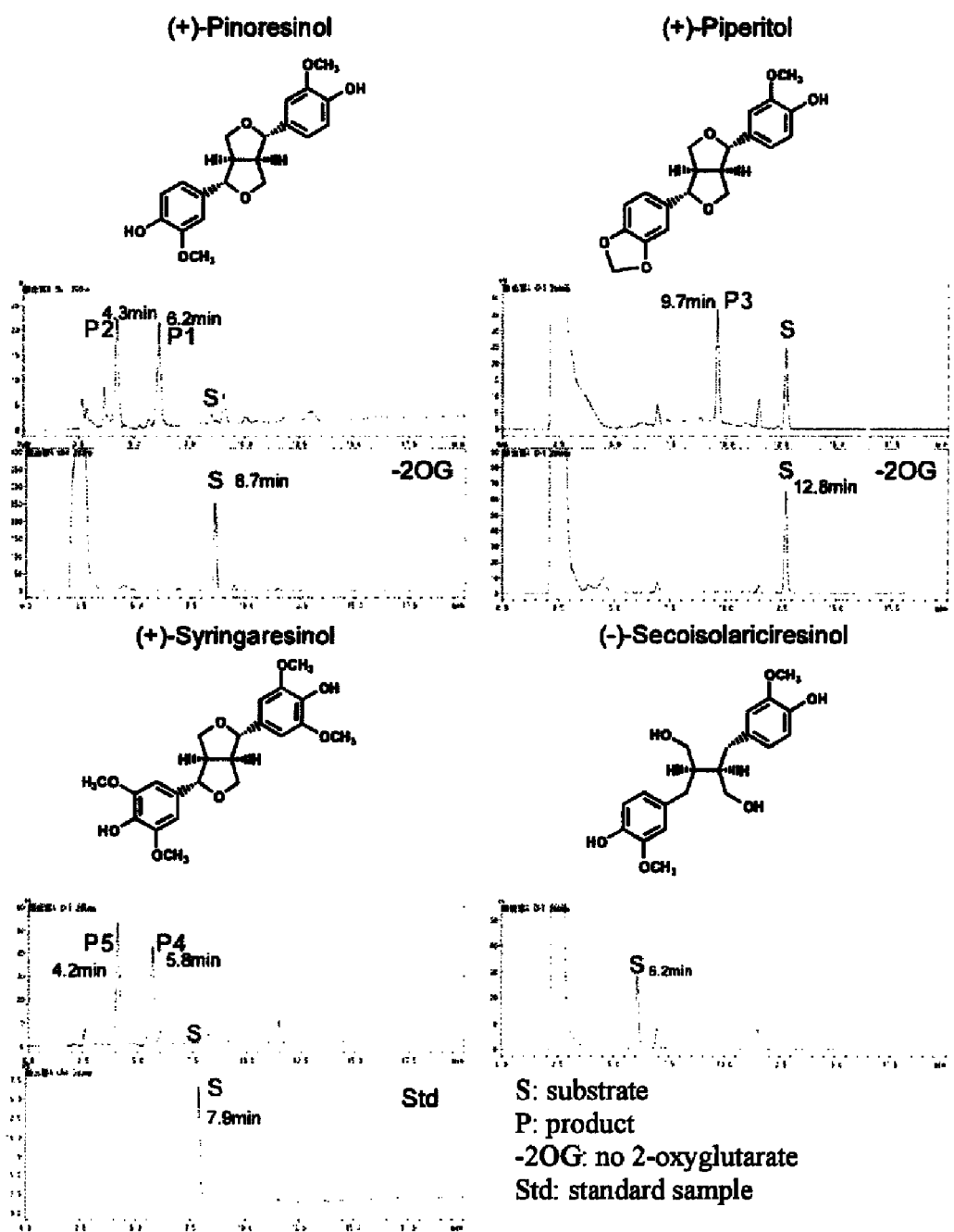
FIG. 2 HPLC Analysis of SiD products
S: substrate
P: product
-2OG: no 2-oxyglutarate
Std: standard sample

FIG. 3 Detection of SiD6 recombinant protein by SDS-PAGE
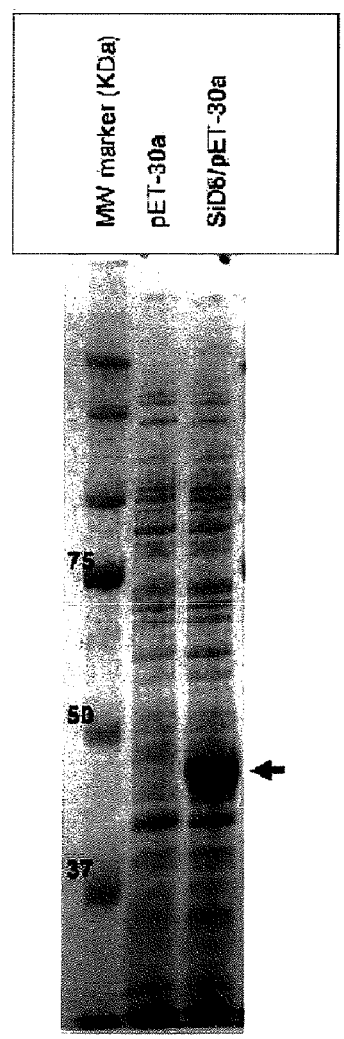

FIG. 4 Signal assignment of P3 (9-hydroxypiperitol) by NMR analysis
|  | $^1H$ $\delta$ | | $J$ Hz | $^{13}C$ $\delta$ |
|---|---|---|---|---|
| 7 | 4.74 | d | 7 | 82.5 |
| 8 | 2.68 | t | 7 | 62.0 |
| 9 | 5.39 | bs |  | 100.7 |
| 1 |  |  |  | 136.2 |
| 2 | 6.91 | d | 1 | 106.2 |
| 3 |  |  |  | 147.3 |
| 4 |  |  |  | 146.4 |
| 5 | 6.87 | d | 8 | 107.9 |
| 6 | 6.83 | brd | 8 | 106.3 |
| OCH$_2$O | 6.00 | s |  | 100.8 |
| 7' | 4.74 | d | 7 | 86.0 |
| 8' | 3.02 | m |  | 53.2 |
| 9'a | 4.10 | dd | 9,6 | 71.3 |
| 9'b | 3.90 | dd | 9,2 | 71.3 |
| 1' |  |  |  | 133.8 |
| 2' | 7.10 | d | 1 | 110.6 |
| 3' |  |  |  | 147.4 |
| 4' |  |  |  | 145.7 |
| 5' | 6.71 | d | 8 | 114.8 |
| 6' | 6.84 | brd | 8 | 118.9 |
| OCH$_3$ | 3.76 | s |  | 55.4 |
FIG. 5 Structure of P3 (9-hydroxylpiperitol)
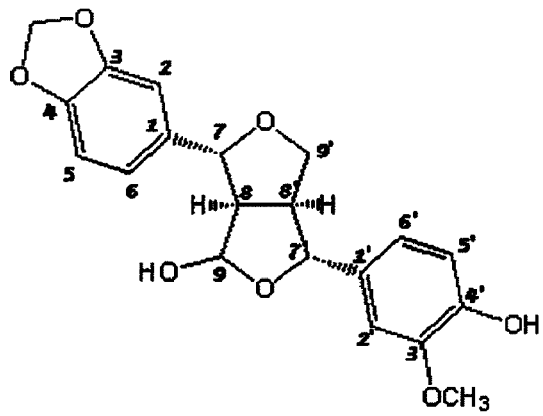

FIG. 6 Hydroxylation of lignans catalyzed by SiD6
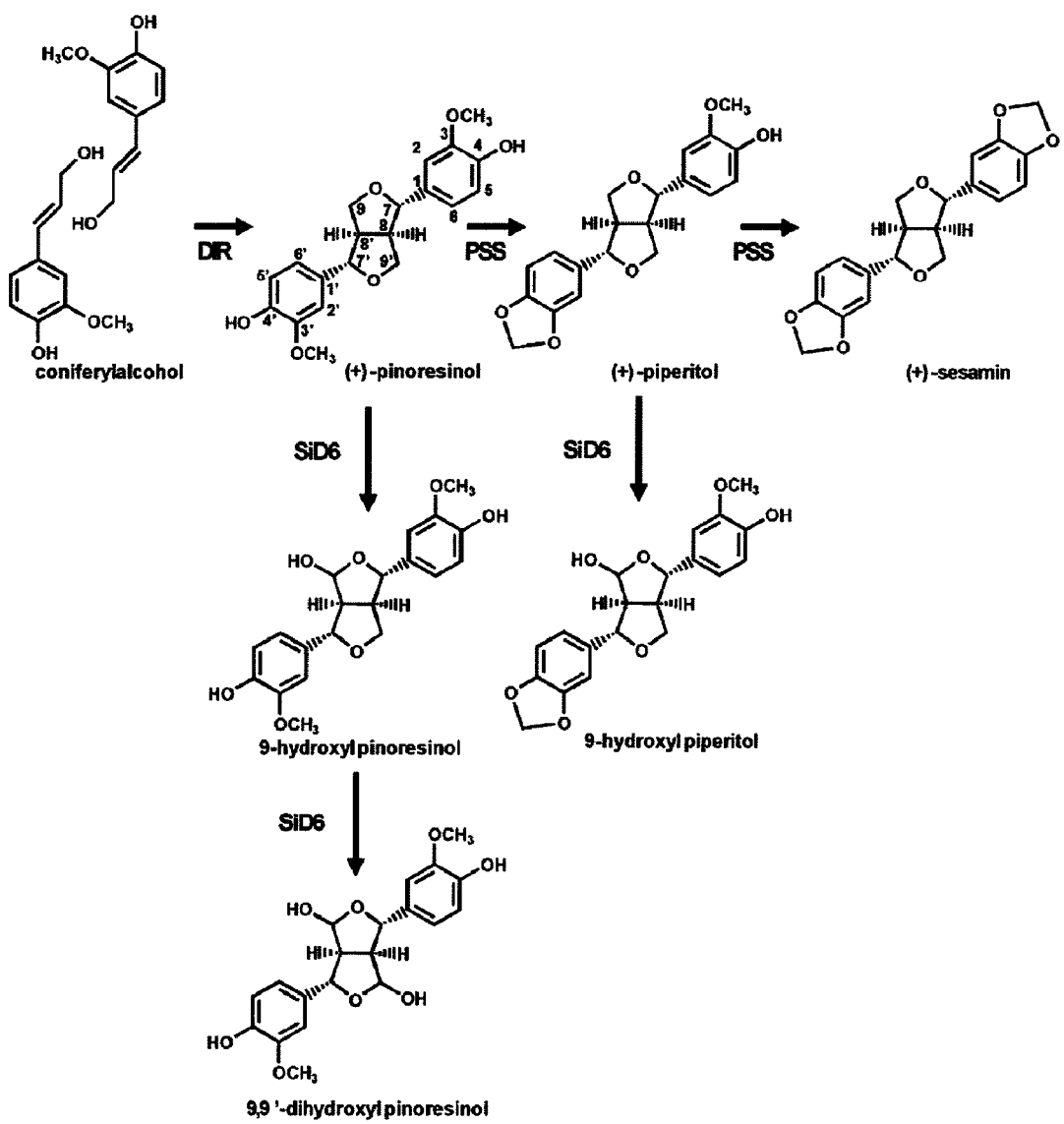
DIR: dirigent protein
PSS: piperitol/sesamin synthase (CYP81Q/SiP189)
SiD6: *Sesamum indicum* 2-OG dioxygenase homolog6

LIGNAN HYDROXYLASE

TECHNICAL FIELD

The present invention relates to an enzyme having an activity of transferring hydroxyl to a lignan and a method for using the enzyme.

BACKGROUND ART

Lignans are secondary metabolites (e.g., sesamin, sesamolin, etc.) in vascular plants and widely distributed in plants. It is reported so far that lignans are contained in the seeds, fruits, cut panicles, tubers and/or tuberous roots, etc. of plants. Lignans are considered to contribute mainly to biological defense mechanisms in plants. In addition to plants, lignans have attracted attention since they have a wide variety of physiological and pharmacological functions in organisms other than plants because of their potent antioxidative effects or the like. Lignans have the structure in which two phenylpropanoid molecules having the $C_6$-$C_3$ skeleton are dimerized, and those with an 8,8' linkage are the most prevalent class of lignans (cf., Lignans, D. C. Ayres and J. D. Loike (1990)).

Representative lignans include (+)-pinoresinol, (+)-sesamin, (+)-sesaminol, (+)-sesamolin and (+)-sesamolinol contained in sesame (Sesamum indicum); (+)-pinoresinol, (−)-arctigenin and (−)-matairesinol contained in forsythia (Forsythia intermedia); (−)-pinoresinol and (−)-lariciresinol contained in Daphne tangutica; (+)-secoisolariciresinol contained in linum (Linum usitatissimum); etc. Molecular structures of these lignans are diverse and classified into 8 subclasses in view of the skeletal structure (cf., Phytochemistry Rev. (2003) 2: 371-390).

Biosynthetic pathways of lignans have been studied, focusing mainly on Sesamum indicum of the family Pedaliaceae, Forsythia intermedia of the family Oleaceae and Linum usitatissimum of the family Linaceae. Some enzymes and genes which catalyze the metabolic pathways are reported. It is reported that among them, pinoresinol synthesized by polymerization of coniferyl alcohol is the first lignan in the biosynthesis and a variety of lignans are synthesized from pinoresinol via biosynthetic pathways specific to individual plant species (cf., J. Wood., Sci. 53, 273-284 (2007), Lignans: biosynthesis and function, Comprehensive natural products chemistry, (1999) 1: 640-713). Piperitol is synthesized by the action of piperitol synthase on (+)-pinoresinol. Pinoresinol is the lignan synthesized at the earliest stage of lignan biosynthetic pathways and therefore is the major lignan distributed in many plants, for example, in plants of the families Asteraceae, Oleaceae, Compositae, Umbelliferae, Thymelaeaceae, Magnoliaceae, Liliaceae and Pinaceae.

As enzymes involved in the biosynthesis of lignans, dirigent proteins which take part in pinoresinol synthesis are reported on Forsythia intermedia, etc. (cf., Non-Patent Literature 6: Plant Physiol., (2000) 123: 453 and Patent Literature 1: Japanese National Publication (Tokuhyo) No. 2001-507931, etc.). As genes for enzymes involved in the lignan biosynthesis and their utilization, there are further reports on the gene for pinoresinol-lariciresinol reductase in Forsythia intermedia (cf., Non-Patent Literature 7: J. Biol. Chem., (1996) 271: 29473 and Patent Literature 1), on the gene for pinoresinol-lariciresinol reductase in Thuja plicata (cf., Non-Patent Literature 8) and recombinant secoisolariciresinol dehydrogenase and the method of its use (cf., Non-Patent Literature 9: J. Biol. Chem., (2001) 276: 12614, Patent Literature 2: Japanese National Publication (Tokuhyo) No. 2002-512790, etc.). Furthermore, the gene for cytochrome P450 enzyme having a piperitol-sesamin synthetic activity from Sesamum indicum and its use are reported (cf., Non-Patent Literature 10: Proc. Nat. Acad. Sci. USA, (2006) 103: 10116 and Patent Literature 3: Japanese National Publication (Tokuhyo) No. 2007-507201).

Lignans are known to undergo a variety of modifications including glycosidation, hydroxylation, methylation, prenylation, etc., after the skeletal formation. The genes for glycosyltransferases having a glycosidation activity on furofuran lignans such as sesaminol, which is one of the sesame lignans, are isolated and their use is reported (cf., Patent Literature 1: Japanese Laid-Open Patent Publication (Tokkai) No. 2006-129728).

It is known that 9-hydroxy derivatives of furofuran lignans represented by pinoresinol are present in Ligularia kanaitizensis belonging to the genus Ligularia of the Asteraceae family or Allamanda neriifolia belonging to the genus Allamanda of the family Compositae, which are native to China (cf., Non-Patent Literature 1: Lignans, D. C. Ayres and J. D. Loike (1990); Non-Patent Literature 2: Phytochemistry, (1988) 27, 575; Non-Patent Literature 3: Indian J. Chem. (1995) 34B, 975, etc.). It is reported that 9-hydroxypinoresinol which is one of 9-hydroxy derivatives has an antioxidative and butyrylcholinesterase activity in an in vivo test, and recently a neuroprotective effect against oxidative damages in the brain (Non-Patent Literature 4: J. Pharmacy and Pharmacology, (2005) 57, 233; Non-Patent Literature 5: Proceedings of the Pakistan Academy of Sciences, (2005) 42, 167; Non-Patent Literature 6: J. Pharm. Pharmacol., (2007) 59: 521, etc.). It is also reported that an anti-HIV-1 reverse transferase (RT) activity is noted for 2-methyl-2-butenoicpinoresinol obtained by further modification of the hydroxy to the ester, and clarification of the biosynthetic pathway is expected (cf., Non-Patent Literature 4: J. Pharmacy and Pharmacology, (2005) 57, 233; Non-Patent Literature 5: Proceedings of the Pakistan Academy of Sciences, (2005) 42, 167; Non-Patent Literature 6: J. Pharm. Pharmacol., (2007) 59: 521, etc.).

Notwithstanding that the utility of lignans having hydroxy is reported as stated above, (+)-larreatricin hydroxylase isolated from chaparral of the family Zygophyllaceae is the only lignan hydroxylase (cf, Non-Patent Literature 7: Proc. Nat. Acad. Sci. USA, (2006) 100: 10641). This enzyme belongs to the polyphenol oxidase (PPO) family, which is one of oxidases in plants (cf., Non-Patent Literature 8: Trends in Plant Science, (2007) 12, 29). In addition to this enzyme family, the oxidase families such as cytochrome P450 enzyme, 2-oxoglutarate-dependent oxygenase, etc. are also known to catalyze the hydroxylation of lignans as well (cf., Non-Patent Literature 9: De Montellano, P. R. O., Cytochrome P450-structure, mechanism, and biochemistry. 3rd edition. Kluwer Academic/Plenum Publishers, NY, (2005) and Non-Patent Literature 10: J. Biol. Chem. (2004) 279, 1206). However, (+)-larreatricin hydroxylase is a hydroxylase for lignans having no oxygen at position 9 (9') of the furan ring, but any enzyme that may catalyze the hydroxylation at position 9 of furofuran lignans represented by pinoresinol still remains unclear. Thus, it has been further desired to acquire genes for lignan oxidase and analyze their functions.

Patent Literature 1: Japanese Laid-Open Patent Publication (Tokkai) No. 2006-129728
Non-Patent Literature 1: Lignans, D. C. Ayres and J. D. Loike (1990)
Non-Patent Literature 2: Phytochemistry, (1988) 27, 575
Non-Patent Literature 3: Indian J. Chem., (1995) 34B, 975
Non-Patent Literature 4: J. Pharmacy and Pharmacology, (2005) 57, 233

Non-Patent Literature 5: Proceedings of the Pakistan Academy of Sciences, (2005) 42, 167
Non-Patent Literature 6: J. Pharm. Pharmacol., (2007) 59: 521
Non-Patent Literature 7: Proc. Nat. Acad. Sci. USA, (2003) 100: 10641
Non-Patent Literature 8: Trends in Plant Science, (2007) 12, 29
Non-Patent Literature 9: De Montellano, P. R. O., Cytochrome P450-structure, mechanism, and biochemistry, 3rd edition, Kluwer Academic/Plenum Publishers, NY. (2005)
Non-Patent Literature 10: J. Biol. Chem. (2004) 279, 1206

DISCLOSURE OF INVENTION

In view of the foregoing circumstances, the present invention has been made. An object of the present invention is to provide an enzyme having a lignan-hydroxylating activity, particularly an enzyme capable of catalyzing the reaction of transferring a hydroxyl group into a lignan, preferably an enzyme capable of catalyzing the hydroxylation of piperitol to 9-hydroxylpiperitol or pinoresinol to 9-hydroxylpinoresinol. More specifically, an object of the present invention is to provide hydroxylated lignan (preferably, a lignan in which the position 9 is hydroxylated; hereinafter a 9-hydroxylignan) by metabolic engineering using an enzyme having the activity of transferring the hydroxyl group to a lignan (preferably, at position 9).

Another object of the present invention is to provide a method for producing plants with an increased or decreased content ratio of a lignan to a hydroxylated lignan by metabolic engineering, thereby to efficiently produce the lignan or hydroxylated lignan.

The present invention relates to a polypeptide having the lignan-hydroxylating activity, a polynucleotide encoding the same, a vector or transformant comprising the polynucleotide, a method for producing the polypeptide having the lignan-hydroxylating activity using the transformant; and so on.

(1) A polypeptide having a lignan-hydroxylating activity, comprising:
  (a) the amino acid sequence of SEQ ID NO: 26;
  (b) an amino acid sequence in which 1 to 15 amino acids are deleted, inserted, substituted and/or added in the amino acid sequence of SEQ ID NO: 26; or,
  (c) an amino acid sequence having at least 80% identity to the amino acid sequence of SEQ ID NO: 26.

(2) The polypeptide having a lignan-hydroxylating activity according to (1) above, comprising
  (a) the amino acid sequence of SEQ ID NO: 26; or,
  (b') an amino acid sequence in which one to several amino acids are deleted, inserted, substituted and/or added in the amino acid sequence of SEQ ID NO: 26.

(3) A polynucleotide which is any one of (a) through (e) below:
  (a) a polynucleotide comprising the nucleotide sequence of SEQ ID NO: 27;
  (b) a polynucleotide encoding a protein comprising the amino acid sequence of SEQ ID NO: 26;
  (c) a polynucleotide encoding a polypeptide in which 1 to 15 amino acids are deleted, inserted, substituted and/or added in the amino acid sequence of SEQ ID NO: 26, and having a lignan-hydroxylating activity;
  (d) a polynucleotide encoding a polypeptide having at least 80% identity to the amino acid sequence of SEQ ID NO: 26 and having a lignan-hydroxylating activity; and,
  (e) a polynucleotide which hybridizes under stringent conditions to a polynucleotide consisting of a nucleotide sequence complementary to the nucleotide sequence of SEQ ID NO: 27, and encoding a polypeptide having a lignan-hydroxylating activity.

(4) The polynucleotide according to (3) above, encoding a polypeptide having a lignan-hydroxylating activity and is any one of (f) through (i) below:
  (f) a polynucleotide consisting of the nucleotide sequence of SEQ ID NO: 27;
  (g) a polynucleotide which hybridizes under stringent conditions to a polynucleotide consisting of a nucleotide sequence complementary to the nucleotide sequence of SEQ ID NO: 27;
  (h) a polynucleotide consisting of a nucleotide sequence having at least 90% identity to the nucleotide sequence of SEQ ID NO: 27; and,
  (i) a polynucleotide in which one to several nucleotides are deleted, inserted, substituted and/or added in the nucleotide sequence of SEQ ID NO: 27.

(5) The polynucleotide according to (3) above, which is a polynucleotide consisting of the nucleotide sequence of SEQ ID NO: 27.

(6) The polynucleotide according to any one of (3) to (5) above, wherein the lignan-hydroxylating activity is hydroxylation at position 9 of a lignan.

(7) An oligonucleotide consisting of a fragment of the polynucleotide according to any one of (3) to (6) above, or a complementary sequence thereof (8) The oligonucleotide according to (7) above, wherein expression of the polypeptide according to (1) or (2) above is inhibited.

(9) A vector comprising the polynucleotide according to (3) through (6) above.

(10) A method for producing a polypeptide, which comprises using the vector according to (9) above.

(11) A transformant having introduced therein the polynucleotide according to any one of (3) through (6) above.

(12) The transformant according to (11) above, wherein the content ratio of a hydroxylated lignan is modified by introducing a lignan and the polynucleotide according to any one of (3) through (6) above.

(13) The transformant according to (11) or (12) above, which is an organism or a progeny thereof, or a tissue derived therefrom.

(14) The transformant according to (13) above, wherein the organism is a plant.

(15) The transformant according to (14) above, wherein the plant is *Sesamum indicum, Forsythia intermedia* or *Linum usitatissimum*.

(16) A method for producing a polypeptide, which comprises using the transformant according to any one of (11) through (15) above.

(17) A method of producing a hydroxylated lignan, which comprises using the transformant according to any one of (11) through (15) above.

(18) The method for producing a hydroxylated lignan according to (17) above, wherein a substrate for the hydroxylated lignan is piperitol or pinoresinol.

(19) A cell comprising the vector according to (9) above.

(20) The cell according to (19) above, which is a cell derived from *Sesamum indicum, Forsythia intermedia* or *Linum usitatissimum*.

(21) A method for producing a polypeptide, which comprises using the cell according to (19) or (20) above.

(22) A method for producing a hydroxylated lignan, which comprises using the cell according to (19) or (20) above.

(23) The method for producing a hydroxylated lignan according to (22) above, wherein a substrate for the hydroxylated lignan is piperitol or pinoresinol.

(24) A method for producing a hydroxylated lignan, which comprises using the polypeptide according to (1) or (2) above.

(25) The method for producing a hydroxylated lignan according to (24) above, wherein a substrate for the hydroxylated lignan is piperitol or pinoresinol.

(26) A foodstuff or industrial product comprising the hydroxylated lignan produced by the production method according to any one of (17), (22) and (24) above.

(27) The foodstuff or industrial product according to (26) above, wherein a substrate for the hydroxylated lignan is piperitol or pinoresinol.

(28) A method of increasing the content of a hydroxylated lignan in an organism, which comprises the step of introducing the polynucleotide according to any one of (3) through (6) above into a lignan-producing organism.

(29) The method according to (28) above, wherein the lignan-producing organism is *Sesamum indicum, Forsythia intermedia* or *Linum usitatissimum*.

(30) The method according to (28) or (29) above, wherein the lignan is piperitol or pinoresinol.

(31) A method of decreasing the content of a hydroxylated lignan in an organism, which comprises the step of introducing the oligonucleotide according to (8) above into a lignan-producing organism.

(32) The method according to (31) above, wherein the lignan-producing organism is *Sesamum indicum, Forsythia intermedia* or *Linum usitatissimum*.

(33) The method according to (31) or (32) above, wherein the lignan is piperitol or pinoresinol.

(34) Compound (9-hydroxylpiperitol) shown by the following formula.

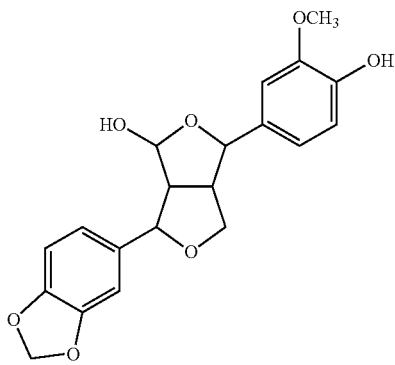

The present invention provides the effects that the amount of a lignan and a hydroxylated lignan in an organism (especially in a plant) can be artificially controlled by using the polypeptide (lignan hydroxylase) in accordance with the present invention. Also, by introducing an additional hydroxyl group into a lignan by using the lignan hydroxylase in accordance with the present invention, the hydroxyl group can be further modified, for example, can be glycosidated or esterified. Based on these effects, a novel physiologically functional substance can be developed according to the present invention.

The present invention can provide the effects that 9-hydroxylpiperitol can be artificially produced from piperitol and 9-hydroxylpinoresinol from pinoresinol by expressing the lignan hydroxylase in accordance with the present invention in a desired organisms using genetic engineering technology. The present invention can further provide the effect of producing a plant and/or microorganism wherein the amounts of a lignan and a hydroxylated lignan can be artificially controlled by expressing the lignan hydroxylase in accordance with the present invention in a desired organism by genetic engineering technology.

BRIEF DESCRIPTION OF DRAWINGS

FIG. 1 shows the expression analysis of SiD genes by RT-PCR.
FIG. 2 shows the HPLC analysis of the SiD6 products.
FIG. 3 shows the results of detection of SiD6 recombinant protein by SDS-PAGE.
FIG. 4 shows the signal assignment of P3 (9-hydroxylpiperitol) by NMR analysis.
FIG. 5 shows the structure of P3 (9-hydroxylpiperitol).
FIG. 6 shows the schematic view of hydroxylation of lignans catalyzed by SiD6.

BEST MODES FOR CARRYING OUT THE INVENTION

The present inventors exhaustively acquired a sesame 2-oxoglutarate (hereinafter abbreviated as 2-OG)-dependent dioxygenase-like gene group (hereinafter referred to as SiD genes) from the sesame seed cDNA library, using as a probe 2-OG-dependent dioxygenase gene belonging to the oxidase family different from a polyphenol oxidase known to be a lignan hydroxylase so far. Each SiD gene acquired was expressed in *Escherichia coli*. After these recombinant proteins were reacted with pinoresinol or piperitol, an enzyme which catalyzes the formation of hydroxylpinoresinol or hydroxylpiperitol by means of HPLC, LC-MS and NMR analyses. The results reveal that SiD6 catalyzes the reaction of forming 9-hydroxylpinoresinol from pinoresinol. The results further reveal that Sid6 catalyzes the reaction of forming 9-hydroxylpiperitol from piperitol. This lignan is a novel hydroxylated lignan not reported to date.

Hereinafter, the polypeptide having the lignan-hydroxylating activity in accordance with the present invention and the polynucleotide encoding the polypeptide as well as use thereof are described in detail.

(1) Polypeptide

The present inventors have found a novel hydroxylase which uses as a main substrate a lignan, especially piperitol and/or pinoresinol, and have come to accomplish the invention. The inventors have further found that the novel hydroxylase above hydroxylates piperitol. Hydroxylpiperitol has not been found so far.

First, the present invention provides the polypeptide having the lignan-hydroxylating activity, comprising (a) the amino acid sequence of SEQ ID NO: 26; (b) an amino acid sequence in which 1 to 15 amino acid residues are deleted, inserted, substituted and/or added in the amino acid sequence of SEQ ID NO: 26; or, (c) an amino acid sequence having at least 80% identity to the amino acid sequence of SEQ ID NO: 26.

As used herein, the term "polypeptide" is interchangeably used with "peptide" or "protein." A "fragment" of the polypeptide is intended to mean a partial fragment of the polypeptide. The polypeptide in accordance with the present invention may be isolated from natural supply sources or may be chemically synthesized.

The term "isolated" polypeptide or protein is intended to mean a polypeptide or protein which has been isolated from its natural environment. For example, the polypeptide and protein produced in host cells by recombination are considered to be isolated as in naturally occurring or recombinant polypeptide and protein substantially purified by optional and appropriate techniques.

The polypeptide in accordance with the present invention embraces a purified natural product, a chemically synthetic product, and a product produced from prokaryotic hosts or eukaryotic hosts (including, e.g., bacterial cells, yeast cells, higher plant cells, insect cells and mammal cells) using recombinant techniques. Depending on the host used in the protocol of recombinant production, the polypeptide in accordance with the present invention may be hydroxylated or non-hydroxylated. In some cases, the polypeptide in accordance with the present invention may further comprise the starting modified methionine residue, as a result of a host-mediated process.

As used herein, the term "lignan-hydroxylating activity" is intended to mean an activity of hydroxylating a lignan (preferably an activity of forming a 9-hydroxylignan), i.e., an activity of transferring a hydroxyl group to a lignan. That is, as used herein, a hydroxylase is interchangeably used with a transhydroxylase.

In one embodiment, the polypeptide in accordance with the present invention is preferably the polypeptide consisting of the amino acid sequence of SEQ ID NO: 26.

In another embodiment, the polypeptide in accordance with the present invention is preferably a mutant of the polypeptide consisting of the amino acid sequence of SEQ ID NO: 26 and having the lignan-hydroxylating activity.

Such mutants include mutants containing deletion, insertion, inversion, repetition and type substitution (e.g., substitution of another residue for a hydrophilic residue; normally, a strongly hydrophobic residue is not substituted for a strongly hydrophilic residue, however). In particular, "neutral" amino acid substitution in the polypeptide hardly affects the activity of the polypeptide in general.

It is well known in the art that some amino acids in the amino acid sequence of the polypeptide may be easily modified without any significant effect on the structure or function of this polypeptide. It is also well known that not only in an artificially modified protein but also in a naturally occurring protein, there are mutants that do not significantly alter the structure or function of the protein.

A person skilled in the art can easily modify one to several amino acids in the amino acid sequence of the polypeptide using well-known techniques. For example, an optional nucleotide in the polynucleotide encoding the polypeptide can be mutated by a known point mutagenesis. Further by designing primers corresponding to optional sites of the polynucleotide encoding the polypeptide, deleted mutants or added mutants can be prepared. Further by using the methods described in the specification, it can be easily assayed if the prepared mutants have a desired activity.

Preferred mutants contain conservative or non-conservative amino acid substitution, deletion or addition, which are preferably silent substitution, addition and deletion, particularly preferably conservative substitution. These mutants do not alter the activity of the polypeptide in accordance with the present invention.

The conservative substitution considered to be representative includes replacement of another amino acid for one amino acid in aliphatic amino acids Ala, Val, Leu and Ile; exchange of the hydroxyl residues Ser and Thr, exchange of the acidic residues Asp and Glu, replacement between the amide residues Asn and Gln, exchange of the basic residues Lys and Arg, and replacement between the aromatic residues Phe and Tyr.

As shown above in detail, a further guidance which amino acid could be phenotypically silent (namely, which amino acid could hardly exert significantly harmful effects on the function) can be found in Bowie, J. U. et al., "Deciphering the Message in Protein Sequences: Tolerance to Amino acid Substitutions," Science 247: 1306-1310 (1990) (which is hereby incorporated by reference).

The polypeptide which is preferred in the present invention is a polypeptide having the lignan-hydroxylating activity and comprising (a) the amino acid sequence of SEQ ID NO: 26, or (b') an amino acid sequence in which one to several amino acids are deleted, inserted, substituted and/or added in the amino acid sequence of SEQ ID NO: 26. As described above, these mutant polypeptides are not limited to polypeptides having artificially induced mutations by publicly known mutant polypeptide production methods but may also be those isolated and purified from naturally occurring polypeptides.

The polypeptide in accordance with the present invention may be any polypeptide wherein the amino acids are bound to each other via peptide bonds, but is not limited thereto and may also be a conjugated polypeptide having a structure other than the polypeptide. As used herein, the "structure other than the polypeptide" includes a sugar chain, an isoprenoid group, etc. but is not particularly limited thereto.

The polypeptide in accordance with the present invention may include an additional polypeptide. The additional polypeptide includes a polypeptide tagged with an epitope such as His, c-Myc, Flag, etc.

The polypeptide in accordance with the present invention may also be in such a state that a polynucleotide encoding the polypeptide in accordance with the present invention is introduced into a host cell and its polypeptide is expressed in the cell, or may be isolated and purified from cells, tissues, etc. Alternatively, the polypeptide in accordance with the present invention may be chemically synthesized.

In another embodiment, the polypeptide in accordance with the present invention may be expressed in a modified form, such as a fusion protein. For example, the region of additional amino acids (tags), particularly charged amino acids, of the polypeptide in accordance with the present invention may be added to the N terminus and/or C terminus of the polypeptide to improve stability and persistence in host cells, during purification, or during subsequent handling and storage. The polypeptide may have a plurality of tags and positions of the respective tags may be discrete or continuous.

The polypeptide according to this embodiment may be added to, e.g., a tag marker (a tag sequence or a marker sequence) at the N terminus or C terminus, which is a sequence encoding a peptide to facilitate purification of a fused polypeptide. Such sequences may be removed prior to final preparation of the polypeptide. In a specific embodiment preferred from this aspect of the present invention, the tag amino acid sequence is a hexahistidine peptide (SEQ ID NO: 47) (e.g., the tag supplied by a pQE vector (Qiagen, Inc.)); among others, many of them are available publicly and/or commercially. As described in, e.g., Gentz, et al., Proc. Natl. Acad. Sci. USA, 86: 821-824 (1989) (which is hereby incorporated by reference), hexahistidine (SEQ ID NO: 47) provides convenient purification for a fusion protein. The "HA" tag is another peptide useful for purification, which corresponds to an epitope derived from the influenza hemagglutinin (HA) protein, described by Wilson et al., Cell, 37: 767 (1984) (which is hereby incorporated by reference). Other such fusion proteins include the polypeptide according to this embodiment, which is fused to Fc at the N or C terminus, or its fragments.

The polypeptide in accordance with the present invention may be recombinantly produced or chemically synthesized, as will be described below in detail.

Recombinant production can be carried out using techniques well known in the art, and can be performed using, for example, the vectors and cells as described below in detail.

Synthetic peptides can be synthesized by known methods used for chemical synthesis. For example, Houghten describes a simple method for synthesis of large numbers of peptides, such as 10-20 mg of 248 different 13-residue peptides representing single amino acid mutants of a segment of the HA1 polypeptide which are prepared in less than 4 weeks and characterized; Houghten, R. A., Proc. Natl. Acad. Sci. USA, 82: 5131-5135 (1985). This "Simultaneous Multiple Peptide Synthesis (SMPS)" process is further described in U.S. Pat. No. 4,631,211 issued to Houghten et al. (1986). In this procedure the individual resins for the solid-phase synthesis of various peptides are contained in separate solvent-permeable packets, which enable the optimal use of the many identical repetitive steps involved in solid-phase methods. A completely manual procedure allows 500-1000 or more syntheses to be conducted simultaneously (Houghten et al., supra, 5134). These literatures are hereby incorporated by reference.

The polypeptide in accordance with the present invention is useful for the method and kit for hydroxylating a lignan to obtain a hydroxylated lignan.

The polypeptide in accordance with the present invention can catalyze the hydroxylation of lignans (especially, piperitol or pinoresinol).

As described above, it is sufficient that the polypeptide in accordance with the present invention contains at least the amino acid sequence of SEQ ID NO: 26. That is, it should be noted that polypeptides consisting of the amino acid sequence of SEQ ID NO: 26 and an optional amino acid sequence having a specific function (e.g., a tag) are included in the present invention. The amino acid sequence of SEQ ID NO: 26 may be connected with the optional amino acid sequence through an appropriate linker peptide.

In addition to the activity that the polypeptide hydroxylates pinoresinol, the polypeptide in accordance with the present invention also has the activity of hydroxylating piperitol. Therefore, the use of the polypeptide should not be limited only to the hydroxylation of pinoresinol to form the hydroxylated product.

More specifically, an object of the present invention is to provide the polypeptide having the activity of hydroxylating lignans, and is not directed to particular methods for producing the polypeptide specifically described herein. Accordingly, it should be noted that polypeptides produced by any method other than those methods fall within the technical scope of the present invention, as far as they have the activity of hydroxylating lignans.

(2) Polynucleotide

The present invention further provides the polynucleotide encoding the polypeptide in accordance with the present invention and having the lignan-hydroxylating activity. Specifically, the present invention provides the polynucleotide which is one of (a) through (e) described below:

(a) a polynucleotide comprising the nucleotide sequence of SEQ ID NO: 27;

(b) a polynucleotide encoding a protein comprising the amino acid sequence of SEQ ID NO: 26;

(c) a polynucleotide encoding a polypeptide in which 1 to 15 amino acids are deleted, inserted, substituted and/or added in the amino acid sequence of SEQ ID NO: 26, and having a lignan-hydroxylating activity;

(d) a polynucleotide encoding a polypeptide having at least 80% identity to the amino acid sequence of SEQ ID NO: 26 and having a lignan-hydroxylating activity; and, (e) a polynucleotide which hybridizes under stringent conditions to a polynucleotide consisting of a nucleotide sequence complementary to the nucleotide sequence of SEQ ID NO: 27, and encoding a polypeptide having a lignan-hydroxylating activity.

As used herein, the term "polynucleotide" is interchangeably used with "gene," "nucleic acid" or "nucleic acid molecule" and is intended to mean a polymeric form of nucleotides. As used herein, the term "base sequence" is interchangeably used with "nucleic acid sequence" or "nucleotide sequence" and is given as the sequence of deoxyribonucleotides (abbreviated as A, G, C and T). Also, the "polynucleotide comprising the nucleotide sequence represented by SEQ ID NO: 1 or a fragment thereof" is intended to mean a polynucleotide comprising a sequence given by the respective deoxynuclotides A, G, C and/or T represented by SEQ ID NO: 1, or a fragmental part thereof The polynucleotide in accordance with the present invention can be present in the form of RNA (e.g., mRNA) or DNA (e.g., cDNA or genomic DNA). The DNA may be double-stranded or single-stranded. Single-stranded DNA or RNA may be a coding strand (also known as a sense strand) or it may be a non-coding strand (also known as an anti-sense strand).

As used herein, the term "oligonucleotide" is intended to mean linked nucleotides of, e.g., several to several tens and interchangeably used with "polynucleotide." In the oligonucleotide, a short string of nucleotides is termed a dinucleotide (dimer) or a trinucleotide (trimer), and a long string of nucleotides is expressed by the number of nucleotides polymerized, such as a 30-mer or a 100-mer. The oligonucleotide may be produced as a fragment of longer polynucleotides or may be chemically synthesized.

The fragment of the polynucleotide in accordance with the present invention is intended to mean a fragment of at least 12 nt (nucleotides), preferably about 15 nt, more preferably 20 nt, much more preferably about 30 nt and most preferably about 40 nt, in length. By the fragment of at least 20 nt in length, it is intended to mean a fragment containing consecutive 20 or more nucleotides from the nucleotide sequence represented by, for example, SEQ ID NO: 1. With reference to the specification, the nucleotide sequence represented by SEQ ID NO: 1 is provided and a person skilled in the art can easily produce a DNA fragment based on SEQ ID NO: 1. For instance, digestion with a restricted endonuclease or ultrasonic shear can be readily used to prepare fragments with various sizes. Alternatively, such fragments can be prepared synthetically. Appropriate fragments (oligonucleotides) are synthesized on an Applied Biosystems Incorporated (ABI, 850 Lincoln Center Dr., Foster City, Calif. 94404) Model 392 synthesizer, etc.

Furthermore, the polynucleotide in accordance with the present invention can be fused to a polynucleotide encoding the aforesaid tag marker (tag sequence or marker sequence) at the 5' or 3' end thereof.

Preferably, the polynucleotide in accordance with the present invention is a polynucleotide encoding the polypeptide having the lignan-hydroxylating activity or its mutant.

The present invention provides a mutant of the polynucleotide, which encodes the polypeptide having the lignan-hydroxylating activity. The "mutant" may occur spontaneously, such as a naturally occurring allelic mutant. By the "allelic mutant" it is intended to mean one of several alternate forms of a gene occupying a given locus on a chromosome of an organism. Non-naturally occurring mutants may be produced, for example, by using mutagenesis techniques well known in the art.

In an embodiment, the polynucleotide in accordance with the present invention is preferably a mutant in which one to several nucleotides are deleted, inserted, substituted or added in the nucleotide sequence of the polynucleotide encoding the polypeptide having the lignan-hydroxylating activity. The mutant may be altered in coding regions, non-coding regions, or both regions. The alteration in the coding regions may produce conservative or non-conservative amino acid deletions, insertions, substitutions and/or additions.

The polynucleotide which is preferred in the present invention is a polynucleotide encoding a polypeptide having a lignan-hydroxylating activity and is any one of (f) through (i) below:

(f) a polynucleotide consisting of the nucleotide sequence of SEQ ID NO: 27;

(g) a polynucleotide which hybridizes under stringent conditions to a polynucleotide consisting of a nucleotide sequence complementary to the nucleotide sequence of SEQ ID NO: 27;

(h) a polynucleotide consisting of a nucleotide sequence having at least 90% identity to the nucleotide sequence of SEQ ID NO: 27; and, (i) a polynucleotide in which one to several nucleotides are deleted, inserted, substituted and/or added in the nucleotide sequence of SEQ ID NO: 27.

In another embodiment, the polynucleotide in accordance with the present invention is preferably an isolated polynucleotide, including a polynucleotide encoding the polypeptide having the lignan-hydroxylating activity, and a polynucleotide, which hybridizes to said polynucleotide, under stringent hybridization conditions.

The polynucleotide which is most preferred in the present invention is a polynucleotide consisting of the nucleotide sequence of SEQ ID NO: 27.

The hybridization may be performed by such a well-known method as described in Sambrook et al., Molecular Cloning, A Laboratory Manual, 2nd Ed., Cold Spring Harbor Laboratory (1989). Higher temperature and lower salt concentration normally result in higher stringency (difficulty of hybridization) so that a more homologous polynucleotide can be acquired. Appropriate temperature for the hybridization varies depending upon nucleotide sequence or length of the nucleotide sequence. Where a DNA fragment consisting of 18 nucleotides encoding 6 amino acids is used as a probe, the temperature is preferably 50° C. or lower.

As used herein, the term "polynucleotide which hybridizes under stringent conditions" is intended to mean a polynucleotide (e.g., a DNA) obtained by means of colony hybridization, plaque hybridization, southern hybridization, etc. using as a probe the whole or part of a polynucleotide consisting of a nucleotide sequence complementary to the nucleotide sequence of SEQ ID NO: 27, or a polynucleotide encoding the amino acid sequence of SEQ ID NO: 26. The hybridization can be performed by such a well-known method as described in Molecular Cloning, 3rd Ed., Current Protocols in Molecular Biology, John Wiley & Sons 1987-1997, etc.

The term "stringent conditions" as used herein may be any of low stringent conditions, moderate stringent conditions or high stringent conditions. "Low stringent conditions" are, for example, conditions under 5×SSC, 5×Denhardt's solution, 0.5% SDS, 50% formamide at 32° C. "Moderate stringent conditions" are, for example, conditions under 5×SSC, 5×Denhardt's solution, 0.5% SDS, 50% formamide at 42° C. "High stringent conditions" are, for example, conditions under 5×SSC, 5×Denhardt's solution, 0.5% SDS, 50% formamide at 50° C. Under these conditions, a polynucleotide (e.g., a DNA) with higher homology is expected to be obtained efficiently at higher temperature, although multiple factors are involved in hybridization stringency including temperature, probe concentration, probe length, ionic strength, time, salt concentration and others, and a person skilled in the art may appropriately select these factors to materialize similar stringency.

When a commercially available kit is used for the hybridization, for example, Alkphos Direct Labeling Reagents (manufactured by Amersham Pharmacia) may be used. In this case, according to the attached protocol, incubation is performed with a labeled probe overnight and the membrane is washed with a primary wash buffer containing 0.1% (w/v) SDS at 55° C., whereby the hybridized polynucleotide (e.g., a DNA) can be detected.

Other polynucleotides that can be hybridized include polynucleotides having 80% or higher, 81% or higher, 82% or higher, 83% or higher, 84% or higher, 85% or higher, 86% or higher, 87% or higher, 88% or higher, 89% or higher; 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity, to the polynucleotide encoding the amino acid sequence of SEQ ID NO: 26, as calculated by homology search software, such as PASTA, BLAST, etc., using default parameters.

The identity between amino acid sequences or nucleotide sequences can be determined using algorithm BLAST by Karlin and Altschul (Proc. Natl. Acad. Sci. USA, 87, 2264-2268, 1990; Proc. Natl. Acad. Sci. USA, 90, 5873, 1993). Programs called BLASTN and BLASTX based on BLAST algorithm have been developed (Altschul, S. F., et al., J. Mol. Biol., 215, 403, 1990). When a nucleotide sequence is sequenced using BLASTN, the parameters are, for example, score=100 and word length=12. When an amino acid sequence is sequenced using BLASTX, the parameters are, for example, score=50 and word length=3. When BLAST and Gapped BLAST programs are used, default parameters for each of the programs are employed.

The present invention further provides the oligonucleotide consisting of a fragment of the polynucleotide described above or its complementary sequence.

Even where the oligonucleotide in accordance with the present invention does not encode the polypeptide for lignan hydroxylation, a person skilled in the art readily understands that the polynucleotide in accordance with the present invention could be used as a primer for polymerase chain reaction (PCR) to produce the polypeptide in accordance with the present invention. Other use of the oligonucleotide in accordance with the present invention that does not encode the polypeptide for lignan hydroxylation includes the following: (1) isolation of the lignan hydroxylase gene from a cDNA library or its allelic mutants or splicing mutants, (2) in situ hybridization (e.g., "FISH") to metaphase chromosomal spreads to provide the precise chromosomal location of the lignan hydroxylase gene (as described in Verma, et al., Human Chromosomes: A Manual of Basic Techniques, Pergamon Press, New York (1988)) and (3) northern blot analysis for detecting the expression of lignan hydroxylase mRNA in particular tissues.

The polynucleotide or oligonucleotide in accordance with the present invention includes not only double-stranded DNA but also single-stranded DNA or RNA such as sense strand and antisense strand, which constructs the double-stranded DNA. The polynucleotide or oligonucleotide in accordance with the present invention can be used as a tool for gene expression manipulation via an antisense RNA mechanism. A decrease of the gene product derived from endogenous gene is observed by the antisense RNA technique. By introducing the oligonucleotide in accordance with the present invention, the level of the polypeptide having the lignan-hydroxylating activity can be reduced so that the content or content ratio of the hydroxylated lignan in a plant can be controlled (increased or decreased). The polynucleotide or oligonucleotide in accordance with the present invention may be those having a sequence from the untranslated region (UTR), a vector sequence (including an expression vector sequence), etc.

A method for acquiring the polynucleotide or oligonucleotide in accordance with the present invention includes various known methods for isolating DNA fragments containing the polynucleotide or oligonucleotide in accordance with the present invention. For example, a probe that specifically hybridizes to a part of the nucleotide sequence of the polynucleotide in the present invention is prepared followed by screening of a genomic DNA library or cDNA library. Such a probe may be a polynucleotide (oligonucleotide) which specifically hybridizes at least to a part of the nucleotide sequence of the polynucleotide in accordance with the present invention or its complementary sequence.

Such a polynucleotide as screened by the hybridization includes a naturally occurring polynucleotide (e.g., a polynucleotide derived from plants such as plants of the Pedaliaceae, Bryophyta, etc.), but may also be a polynucleotide derived from other than plants.

An alternative method of acquiring the polynucleotide in accordance with the present invention further includes a method using PCR. This PCR amplification method comprises, e.g., the step of preparing primers using the 5'-end and/or 3'-end sequences (or their complementary sequences) of cDNA of the polynucleotide in accordance with the present invention and the step of amplifying by PCR using these primers as template of genomic DNA (or cDNA), etc. By using this method, DNA fragments containing the polynucleotide in accordance with the present invention can be acquired in large quantities.

The source of supply to acquire the polynucleotide in accordance with the present invention is not particularly limited but includes preferably biological materials containing piperitol or pinoresinol. As used herein, the term "biological material" is intended to mean a biological sample (a tissue sample or cell sample obtained from an organism). In EXAMPLES described below, *Sesamum indicum* is employed but not limited thereto.

By using the polynucleotide in accordance with the present invention, the polypeptide having the lignan-hydroxylating activity can be synthesized in transformants or cells.

By using the polynucleotide in accordance with the present invention, an organism that expresses the polypeptide having the lignan-hydroxylating activity can be readily detected by detecting the hybridizing polynucleotide.

The oligonucleotide in accordance with the present invention can be utilized as a hybridization probe for detecting the polynucleotide encoding the polypeptide having the lignan-hydroxylating activity or as a primer for amplifying the said polynucleotide, whereby an organism or tissue that expresses the polypeptide having the lignan-hydroxylating activity can be readily detected. Further by using the aforesaid oligonucleotide as an antisense oligonucleotide, the expression of the polypeptide having the lignan-hydroxylating activity can be repressed in the organism described above, or its tissues or cells.

In the polynucleotide in accordance with the present invention, the polypeptide encoded by said polynucleotide has not only the activity of hydroxylating pinoresinol but also the activity of hydroxylating piperitol. Thus, use of the polynucleotide in accordance with the present invention should not be limited only to the hydroxylation of pinoresinol to produce these hydroxylated products (e.g., 9-hydroxylated product).

In other words, the object of the present invention is to provide the polynucleotide encoding the polypeptide, which has the activity to hydroxylate piperitol or pinoresinol, and the oligonucleotide, which hybridizes to the polynucleotide, but is not directed to particular methods for producing the polynucleotides and oligonucleotides specifically described herein, and so on. It should thus be noted that such polynucleotides encoding the polypeptide having the activity to hydroxylate piperitol or pinoresinol, which are acquired by methods other than those described above, are also within the technical scope of the present invention.

(3) Use of the Polypeptide or Polynucleotide in Accordance with the Invention

The present invention further provides the method for controlling (increasing or decreasing) the amount of a lignan or hydroxylated lignan in an organism (preferably, a plant) by using the polypeptide or polynucleotide in accordance with the present invention, and use of the controlled organism (preferably, a plant).

(A) Vector

The present invention provides a vector which is used to produce the polypeptide having the lignan-hydroxylating activity. The vector in accordance with the present invention may be a vector used for in vitro translation or a vector used for recombinant expression.

The vector in accordance with the present invention is not particularly limited, as far as the vector comprises the polynucleotide in accordance with the present invention. For example, the vector includes a recombinant expression vector inserted with cDNA of the polynucleotide encoding the polypeptide having the lignan-hydroxylating activity, and the like. The method of producing the recombinant expression vector includes a method which comprises using a plasmid, phage or cosmid, etc., but is not particularly limited thereto.

The vector is not particularly limited to specific kinds but such a vector that can be expressed in host cells may be appropriately chosen. That is, a promoter sequence is appropriately chosen to ensure the expression of the polynucleotide in accordance with the present invention depending on kind of host cells. This promoter and the polynucleotide in accordance with the present invention are incorporated into various plasmids, etc., and the vectors thus obtained may be used as expression vectors.

The expression vector in accordance with the present invention contains expression regulatory domains (e.g., a promoter, a terminator and/or a replication origin, etc.) depending upon a biological species of the host to be introduced. The promoter for bacteria used includes a conventional promoter (e.g., a trc promoter, a tac promoter, a lac promoter, etc.). As the promoter for yeast, a glyceraldehyde 3-phosphate dehydrogenase promoter, a PHO5 promoter, etc. may be used. The promoter for filamentous fungi includes, for example, promoters of amylase, trp C, etc. The promoter for animal cell hosts includes a viral promoter (e.g., SV40 early promoter, SV40 late promoter, etc.). The expression vector may be prepared by conventional methods using restriction enzymes and/or ligases, etc. The host cells may be transformed with the expression vector according to conventional procedures.

After the host transformed using the expression vector described above is incubated, cultivated or raised, the objective protein can be recovered and purified from the culture broth or the like in a conventional manner (e.g., filtration, centrifugation, cell lysis, gel filtration chromatography, ion exchange chromatography, etc.).

The expression vector preferably contains at least one selection marker. Such a marker includes dihydrofolate reductase or neomycin resistance for eukaryotic cell culture and tetracycline or ampicillin resistance genes for the culture in *Escherichia coli* and other bacteria.

Using the selection marker described above, it can be confirmed whether or not the polynucleotide in accordance with the present invention is introduced into a host cell and further whether or not the polynucleotide is certainly expressed in a host cell. Alternatively, the polypeptide in accordance with the present invention may be expressed as a fused polypeptide; for example, a green fluorescent polypeptide (GFP) derived from jelly fish or *Aequorea victoria* may be used as a marker to express the polypeptide in accordance with the present invention in the form of a GFP-fused polypeptide.

The host cells described above are not particularly limited and various cells hitherto known may be advantageously used. Specific examples include, but not limited to, bacteria such as *Escherichia coli*, etc., yeasts (*Saccharomyces cerevisiae, Schizosaccharomyces pombe*), *Caenorhabditis elegans* or oocytes of *Xenopus laevis*, etc. Culture media and conditions suitable for the host cells described above are well known in the art.

Methods for introducing the vectors described above, namely, transformation methods are not particularly limited either, and such transformation can be advantageously carried out by any method known in the art. These methods include the electroporation, calcium phosphate, liposome and DEAE-dextran methods, etc. Where the polypeptide in accordance with the present invention is transiently expressed in insects, an expression system using baculovirus may be employed.

By using the vector in accordance with the present invention, the polynucleotide described above can be introduced into organisms or cells, and the polypeptide having the lignan-hydroxylating activity can be expressed in the organisms or cells. In addition, the vector in accordance with the present invention can be used in a cell-free protein synthesis system to synthesize the polypeptide having the lignan-hydroxylating activity.

As described above, the vector in accordance with the present invention comprises at least the polynucleotide encoding the polypeptide in accordance with the present invention. It should thus be noted that vectors other than the expression vectors are also within the technical scope of the present invention.

That is, the object of the present invention is to provide the vector comprising the polynucleotide encoding the polypeptide in accordance with the present invention, but not only to provide the respective vector and cell species specifically described herein and methods of producing these vectors or introducing these cells. It should thus be noted that vectors obtained by other methods of producing vectors using vector species other than those described above are also within the technical scope of the present invention.

(B) Transformant or Cell

The present invention provides transformants or cells in which the polynucleotide encoding the polypeptide having the lignan-hydroxylating activity described above is introduced. As used herein, the term "transformant" is intended to mean not only a tissue or organ but also an individual organism.

Methods of preparing (producing) transformants or cells are not particularly limited, and include, for example, the aforesaid method which involves transformation by incorporating a recombinant vector into a host. Organisms to be transformed are not particularly limited, and examples include various microorganisms, plants or animals illustratively given for the host cells described above.

The transformants or cells in accordance with the present invention are characterized in that the compositions are altered from those in naturally occurring lignans and/or hydroxylated lignans. The transformants or cells in accordance with the present invention are preferably plants or their progeny, or tissues derived therefrom, more preferably, *Sesamum indicum, Forsythia intermedia* or *Linum usitatissimum*. In these transformants or cells, the content of hydroxylated lignans in lignan-producing organisms can be increased or decreased by the method in accordance with the present invention for controlling the content of hydroxylated lignans.

In an embodiment, the transformant in accordance with the present invention can be a plant transformant. The plant transformant according to this embodiment can be acquired by introducing a recombinant vector comprising the polynucleotide in accordance with the present invention into a plant in such a manner that the polypeptide encoded by the said polynucleotide can be expressed therein.

Where the recombinant expression vector is used, the recombinant expression vector used to transform the plant is not particularly limited as far as the vector is capable of expressing the polynucleotide in accordance with the present invention in a plant. Examples of such vectors include a vector bearing a promoter (e.g., a 35S promoter of cauliflower mosaic virus) capable of constitutively expressing the polynucleotide in plant cells, and a vector bearing a promoter (e.g., a metallothionein promoter) which is inducibly activated by external stimulation.

Plants which are the target of transformation in the present invention may be any of entire plant bodies, plant organs (e.g., leaves, petals, stems, roots, seeds, etc.), plant tissues (e.g., epidermis, phloem, parenchyma, xylem, vascular bundles, palisade tissues, spongy tissues, etc.) or plant culture cells, or various types of plant cells (e.g., a culture cell suspension), protoplasts, leaf slices, callus, and the like. Specific examples of plant species which are used for the transformation include, but are not limited to, those belonging to the Monocotyledoneae or the Dicotyledoneae.

For the transformation of genes into plants, conventional transformation methods known to those skilled in the art are used (e.g., the *Agrobacterium* method, gene gun, the PEG method, the electroporation method, etc.). For example, the *Agrobacterium*-mediated method and the method of directly introducing genes into plant cells are well known. Where the *Agrobacterium* method is used, the plant expression vector constructed is introduced into an appropriate *Agrobacterium* strain (e.g., *Agrobacterium tumefaciens*), followed by infection of aseptically cultured leaf discs with this strain according to the leaf disc method (Hirobumi Uchimiya, Manuals for Plant Gene Manipulation (1990), 27-31, Kodansha Scientific Co., Ltd., Tokyo). Thus, the transgenic plant can be obtained. The method of Nagel, et al. (Microbiol. Lett., 67, 325 (1990)) may be used as well. This method involves introducing first, e.g., an expression vector into *Agrobacterium* and then introducing the transformed *Agrobacterium* into plant cells or plant tissues according to the method described in Plant Molecular Biology Manual (S. B. Gelvin, et. al., Academic Press Publishers). Herein, the term "plant tissue" includes callus, which is obtained by culturing plant cells. Where the transformation is carried out by using the *Agrobacterium* method, binary vectors (pBI121, pPZP202, etc.) can be used.

For the direct introduction of genes into plant cells or plant tissues, the electroporation method and the gene gun method are known. When the gene gun is used, plant bodies, plant organs or plant tissues per se may be used as they are, or may be used after preparation of slices, or after preparation of protoplasts. The samples thus prepared can be treated using a gene transfer apparatus (e.g., PDS-1000 (BIO-RAD, Inc.), etc.). The treatment conditions vary depending upon type of the plant or sample. Normally, the sample is treated under a pressure of about 450-2000 psi at a distance of about 4-12 cm.

The cells or plant tissues in which the gene is introduced are first selected by chemical resistance such as hygromycin resistance, etc. and then regenerated into plant bodies in a conventional manner. Regeneration of plant bodies from the transformant cells can be performed by methods known to those skilled in the art, depending upon kind of plant cells.

Where a plant culture cell is used as a host, the transformation is preformed by introducing a recombinant vector into culture cells by the gene gun method, the electroporation method, etc. Callus, shoots, hairy roots, etc. resulted from the transformation can be used directly in cell culture, tissue culture or organ culture. Furthermore, they can be regenerated into plant bodies by conventional plant tissue culture methods through the administration of plant hormones (e.g., auxin, cytokinin, gibberellin, abscisic acid, ethylene, brassinolide, etc.) at appropriate concentrations.

Whether or not the gene has been introduced into the host can be confirmed by PCR, Southern hybridization, northern hybridization, or the like. For example, a DNA is prepared from the transgenic plant and DNA-specific primers are then designed for PCR. The PCR can be performed under the same conditions as used for the preparation of plasmids described above. Subsequently, the amplified product is subjected to agarose gel electrophoresis, polyacrylamide gel electrophoresis, capillary electrophoresis, etc. and stained with ethidium bromide, SYBR Green solution, etc. By detecting the amplified product as a single band, it can be confirmed that the transformation has occurred. Alternatively, PCR may be performed using primers previously labeled with a fluorescent dye or the like, and, the amplified product can be detected. A method which involves immobilizing the amplification product to a solid phase such as a microplate to enable confirmation of the amplified product by means of fluorescence or enzyme reactions, or the like, may be used as well.

Once the transgenic plant wherein the polynucleotide in accordance with the present invention has been incorporated into the genome is acquired, its progeny can be obtained by sexual or asexual reproduction of the plant body. Furthermore, the plant body can be mass-produced by acquiring from the plant body or its progeny or clones thereof, e.g., seeds, fruits, cut panicles, tubers, tuberous roots, strains, callus, protoplasts, etc., and then using them as the origin. Accordingly, the present invention also encompasses the plant body in which the polynucleotide in accordance with the present invention is expressibly introduced, or progenies of the plant body having the same property as in the plant body, and tissues derived therefrom.

The transformation methods for various plants are already reported. Examples of the transgenic plants in accordance with the present invention include, but not be limited to, sesame, rice plant, tobacco, barley, wheat, rapeseed, potato, tomato, poplar, banana, eucalyptus, sweet potato, soybean, alfalfa, lupinus, corn, cauliflower, rose, chrysanthemum, carnation, snapdragon, cyclamen, orchid, Prairie gentian, freesia, gerbera, gladiolus, gypsophila, kalancoe, lily, pelargonium, geranium, petunia, torenia, tulip, *Forsythia intermedia, Arabidopsis thaliana, Lotus japonicus*, and so on.

In a preferred embodiment, the transformant in accordance with the present invention can be prepared using *Sesamum indicum*. The method of preparing the transformant of *Sesamum indicum* includes such a known method as described in, for example, T. Asamizu: Transformation of sesame plants using MAT vector system: introduction of fatty acid desaturase genes, Sesame Newsletter, 16: 22-25 (2002). For the transformation of *Forsythia intermedia*, a known method as described in Carlo Rosati, et al., Regeneration and *Agrobacterium*-mediated transformation of *Forsythia x intermedia* "Spring Glory" is used.

By using the transgenic *Sesamum indicum* and *Forsythia intermedia* thus acquired, hydroxylated lignans are produced in the *Sesamum indicum*. Thus, the hydroxylated lignans (hydroxylpiperitol and/or hydroxylpinoresinol) can be produced at low costs by an environment-friendly production process.

In another preferred embodiment, a tobacco plant can be advantageously used as the transformant in accordance with the present invention. Tobacco is a typical plant which is readily transformed as in petunia, etc. and is capable of regenerating from a cell wall-removed single cell (protoplast) into a single plant body. The regenerated single plant body does not result in a chimeric pattern unlike the single body derived from multiple cells so that its transformants can be efficiently produced.

A preferred example of the method for transformation of tobacco is the leaf disc method. According to this method, operations are easy and multiple independent transformants can be obtained from a single leaf disc. The method for transformation is described in, e.g., "SHIN-SEIBUTSU KAGAKU JIKKEN-NO-TEBIKI (New Guidance of Biochemical Experiment) 3: Isolation/Analysis of Nucleic Acid and Genetic Experimentation, published by Kagaku Dojin, 1996."

Specifically, a leaf disc is excised from an aseptically cultivated tobacco leaf on a sterile Petri dish and the leaf disc cut is preincubated in a NB medium. Next, the preincubated leaf disc is impregnated with a solution of *Agrobacterium*-infected bacteria for co-incubation. The leaf disc is embedded in a NB medium supplemented with carbenicillin and kanamycin and subcultured until shoots generate via callus formation from the leaf disc to obtain the shoots. When the shoots grow up and distinction becomes clear between the stems and leaves, the shoots are excised from the stems and transferred to a MS medium free of any antibiotic or any hormone. After the excised shoots produce roots, the roots are cultivated in a greenhouse. The shoots are then transferred to a hormone-supplemented medium to promote rooting. At the same time, a part of the leaves are excised from the shoots and transplanted to an assay medium supplemented with carbenicillin and kanamycin. Approximately 10 days after the transplantation, the leaves which induce callus are regarded as kanamycin-resistant individuals and thus recovered, whereas the leaves which turn brown are regarded as kanamycin-sensitive individuals and thus discarded.

By using the transgenic tobacco thus obtained, the hydroxylated lignan is produced within the tobacco and the hydroxylated lignan (hydroxylpiperitol and/or hydroxylpinoresinol) can thus be produced at low costs by an environment-friendly production process.

In yet another preferred embodiment, a rice plant can be advantageously employed as the transformant in accordance with the present invention. An embodiment for preparing the rice transformant is described below.

The polynucleotide in accordance with the present invention is introduced into binary vector pPZP202 bearing a hygromycin-resistant gene to construct the transformed vector. The polynucleotide in accordance with the present invention is operably linked to promoter CaMV35S in-frame.

Using the transformed vector obtained, *Agrobacterium tumefaciens* EHA101 strain is transformed by electroporation under selection with 50 mg/l kanamycin and hygromycin. The resulting *Agrobacterium* transformant is stored frozen until use.

Brown rice grains are prepared by removing lemmas from wild-type seeds, sterilized with 70% ethanol for 3 minutes and then washed 3 times with sterilized distilled water. The grains are further sterilized with 50% sodium hypochlorite for 30 minutes and then washed 5 times with sterile distilled water. The brown rice grain is placed on a callus induction medium containing N6 medium (Chu et al., 1975, Sci. Sinica, 18, 659-668) supplemented with 30 g/l sucrose, 0.3 g/l Casamino acid, 2.8 g/l proline and 2.0 mg/l 2,4-D, which is solidified with 4.0 g/l Gelrite. Prior to autoclaving, pH of the medium is adjusted to 5.8. The brown rice grain is grown at 28° C. for 4 weeks in bright light to produce the callus having a size of about 5 mm. This callus is used for *Agrobacterium* infection.

The *Agrobacterium* stored frozen in glycerol is cultured on an AB medium (Chilton et al., 1974, Proc. Natl. Acad. Sci. USA, 71, 3672-3676) supplemented with 20 mg/l kanamycin, 50 mg/l hygromycin and 100 mg/l spectinomycin, which pH is adjusted to 7.2. The medium is then solidified with 15 g/l agar, followed by incubation at 28° C. for 3 days in the dark. The *Agrobacterium* bacterial cells are collected and suspended in liquid AAM medium (Hiei, et al., 1994) supplemented with 10 mg/l acetosyringone (Hiei, et al., 1994, Plant J., 6, 271-282). The callus described above is immersed in the resulting suspension for 2 minutes and blotted on a sterile paper towel to remove excess moisture. The callus is then transferred to the 10 mg/l acetosyringone-containing callus induction medium described above. Co-cultivation is carried out at 28° C. for 3 days for *Agrobacterium* infection. The infected callus obtained is washed 10 times with sterile distilled water and finally once with sterile distilled water containing 500 mg/l carbenicillin to remove excess moisture with a sterile paper towel. This callus is cultivated at 28° C. for 2 weeks in the callus induction medium described above supplemented with 10 mg/l acetosyringone, 50 mg/l hygromycin and 300 mg/l carbenicillin, followed by further cultivation in the callus induction medium supplemented with 50 mg/l hygromycin and 100 mg/l carbenicillin for 4 weeks. Hygromycin-resistant callus is selected and transferred to a regeneration medium containing a MS basal medium (Murashige and Skoog, 1962, Physiol. Plant., 15, 473-497), pH 5.8, supplemented with 30 g/l sucrose, 30 g/l sorbitol, 2 g/l Casamino acid, 2.2 mg/l kinetin, 1.0 mg/l NAA, 100 mg/l carbenicillin, 50 mg/l hygromycin and 4 g/l Gerlite.

The transformant thus obtained can be readily regenerated in a hygromycin-containing regeneration medium and transferred to soil for cultivation.

By using the transgenic rice plant thus obtained, the hydroxylated lignans are produced within the rice plant, and the 1 hydroxylated lignans (hydroxylpiperitol and/or hydroxylpinoresinol) can be produced at low costs by an environment-friendly production process.

The transformant in accordance with the present invention can produce the hydroxylated lignans by introducing the aforesaid polynucleotide therein, as far as an organism contains lignans (especially pinoresinol or piperitol), irrespective of the species of organism.

By using the transformant wherein a recombinant expression vector comprising the polynucleotide encoding the polypeptide in accordance with the present invention is introduced, the transformant can catalyze the reaction of hydroxylating endogenous lignans present in organisms such as plants. Thus, the hydroxylated lignans can be mass-produced at low costs by an environment-friendly production process. In addition, the present invention can provide inexpensive foodstuff or industrial products through the mass-production of hydroxylated lignans.

The polypeptide which catalyzes the reaction for lignan hydroxylation can be provided at low costs under environment-friendly conditions, using the transformant in accordance with the present invention.

In an embodiment, the cells in accordance with the present invention can be a variety of bacterial cells. The cells according to this embodiment are acquired by introducing a recombinant vector comprising the polynucleotide in accordance with the present invention into cells in such a manner that the polypeptide encoded by the polynucleotide can be expressed.

Prokaryotes or eukaryotes can be used as hosts. As the prokaryotic host, there may be used bacteria belonging to, for example, the genus *Escherichia* (e.g., *Escherichia coli*, etc.), bacteria belonging to, for example, the genus *Bacillus* (e.g., *Bacillus subtilis*, etc.). As the eukaryotic host, there may be used lower eukaryotes (e.g., eukaryotic microorganisms such as yeast, filamentous fungi, etc.). The yeast includes microorganisms belonging to the genus *Saccharomyces* (e.g., *Saccharomyces cerevisiae*, etc.) and the filamentous fungi include microorganisms belonging to the genus *Aspergillus* (e.g., *Aspergillus oryzae, Aspergillus niger*, etc.), and microorganisms belonging to the genus *Penicillium*. Animal cells or plant cells can be used as hosts. The animal cells include cells from mice, hamsters, monkeys, humans, etc. In addition, insect cells (e.g., silkworm cells or silkworm imagines) can also be used as hosts.

According to the disclosure in the specification, a person skilled in the art can readily understand that once a recombinant expression vector comprising the polynucleotide encoding the polypeptide having the lignan-hydroxylating activity is introduced, the lignan-hydroxylating capability can be imparted to organisms over a wide range from bacteria to higher plants.

Where an organism contains a lignan (especially pinoresinol or piperitol), irrespective of the species of organism, the cells in accordance with the present invention can produce the hydroxylignan by introducing the aforesaid polynucleotide therein.

Using the cells wherein a recombinant expression vector comprising the polynucleotide encoding the polypeptide in accordance with the present invention, the lignan hydroxylation can be catalyzed within the cells. Thus, the hydroxylated lignan can be mass-produced at low costs by an environment-friendly production process. In addition, the present invention can provide inexpensive foodstuff or industrial products through the mass-production of hydroxylated lignans.

The polypeptide which catalyzes the lignan hydroxylation can be provided at low costs under environment-friendly conditions, by using the cells in accordance with the present invention.

As described above, the transformants or cells in accordance with the present invention work satisfactorily as far as at least the polynucleotide encoding the polypeptide in accordance with the present invention is introduced therein. It should thus be noted that transformants or cells formed by means other than the recombinant expression vector are also within the technical scope of the present invention.

As described above, the polypeptide in accordance with the present invention has the activity of hydroxylating piperitol, in addition to the activity of hydroxylating pinoresinol. Accordingly, use of the polypeptide or cells in accordance with the present invention should not be limited only to the hydroxylation of pinoresinol to produce these hydroxylated products.

In short, the object of the present invention is to provide the transformant or cell wherein the polynucleotide encoding the polypeptide in accordance with the present invention is introduced, and is not only to provide the respective vector species specifically described herein or methods of introducing the same. It should thus be noted that transformants or cells acquired using vector species and cell species other than those described above as well as other methods of preparing vectors or introducing cells are also within the technical scope of the present invention.

(C) Method of Producing Polypeptide

The present invention provides the method of producing the polypeptide in accordance with the present invention. By using the method of producing the polypeptide in accordance with the present invention, the polypeptide which catalyzes the lignan hydroxylation can be provided at low costs under environment-friendly conditions. Further by using the method of producing the polypeptide in accordance with the present invention, the polypeptide which catalyzes the lignan hydroxylation can be readily produced.

In the method of producing the polypeptide according to an embodiment of the present invention, the vector comprising the polynucleotide encoding the polypeptide of the present invention is used.

In the method for producing the polypeptide according to an embodiment of the present invention, it is preferred to use the vector described above in a cell-free protein synthesis system. Where the cell-free protein synthesis system is used, various kits commercially available may be employed. Preferably, the method of producing the polypeptide in accordance with the embodiment comprises the step of incubating the vector described above and a solution for the cell-free protein synthesis.

In the method for producing the polypeptide according to another embodiment of the present invention, it is preferred to use a recombinant expression system. Where the recombinant expression system is used, there may be adopted a method which involves incorporating the polynucleotide in accordance with the present invention into a recombinant expression vector, expressibly introducing the vector into a host by known methods, and purifying the polypeptide resulting from translation in the host; and so on. The recombinant expression vector may be or may not be a plasmid, so long as the objective polynucleotide can be introduced into the host. Preferably, the method of producing the polypeptide according to this embodiment comprises the step of introducing the vector described above into a host.

Where an exogenous polynucleotide is introduced into a host as described above, it is preferred that the expression vector has a promoter having incorporated therein to function in a host so as to express the exogenous polynucleotide. Though methods for purification of the polypeptide recombinantly produced vary depending upon host used and property of the polypeptide, the target polypeptide can be purified relatively easily by using a tag, etc.

Preferably, the method of producing the polypeptide according to this embodiment further comprises the step of purifying the aforesaid polypeptide from the extract of cells or tissues having the polypeptide in accordance with the present invention. The step of purifying the polypeptide preferably comprises, but is not limited to, preparing a cell extract from cells or tissues by well known methods (e.g., a method which comprises disrupting cells or tissues, centrifuging and recovering soluble fractions), followed by purifying the polypeptide from the cell extract by well known methods (e.g., ammonium sulfate or ethanol precipitation, acid extraction, anion or cation exchange chromatography, phosphocelulose chromatography, hydrophobic interaction chromatography, affinity chromatography, hydroxyapatite chromatography and lectin chromatography). Most preferably, high performance liquid chromatography (HPLC) is employed for purification.

In the method of producing the polypeptide according to yet another embodiment, the polypeptide in accordance with the present invention is purified from cells or tissues which naturally express the polypeptide in accordance with present invention. Preferably, the method of producing the polypeptide according to this embodiment comprises the step of identifying the cells or tissues naturally expressing the polypeptide in accordance with the present invention using the oligonucleotide described above. More preferably, the method of producing the polypeptide according to this embodiment further comprises the aforesaid step of purifying the polypeptide.

In yet further embodiment, the method of producing the polypeptide in accordance with the present invention is characterized by chemically synthesizing the polypeptide in accordance with the present invention. A person skilled in the art can readily understand that the polypeptide in accordance with the present invention can be chemically synthesized by applying well known chemical synthesis technology to the amino acid sequence of the polypeptide in accordance with the present invention described herein.

As described above, the polypeptide acquired by the method of producing the polypeptide in accordance with the present invention may be a naturally occurring mutant polypeptide or an artificially produced mutant polypeptide.

Methods of producing the mutant polypeptide are not particularly limited. The mutant polypeptide can be produced by well known methods of producing mutant polypeptides, for example, site-specific mutagenesis (see, e.g., Hashimoto-Gotoh, Gene, 152, 271-275 (1995)), a method of producing mutant polypeptides which involves introducing point mutations into nucleotide sequences using PCR, a method of producing mutants by transposon insertion, etc. Commercially available kits may also be used to produce the mutant polypeptide.

As described above, the polypeptide in accordance with the present invention may be produced by known conventional techniques, at least, based on the amino acid sequence of the polypeptide having the lignan-hydroxylating activity, or the nucleotide sequence of the polynucleotide encoding the polypeptide having the lignan-hydroxylating activity.

That is, the object of the present invention is to provide the method of producing the polypeptide having the lignan-hydroxylating activity. It should thus be noted that production methods further comprising steps other than the various steps described above are also within the technical scope of the present invention.

(D) Method of Producing Hydroxylated Lignan

To date, the production of lignans and hydroxylated lignans has been relied on extraction from plants and thus involves difficulties in mass production, etc. According to the present invention, lignans and hydroxylated lignans can be mass-produced at low costs.

The present invention provides the method of producing hydroxylated lignans using organisms or cells capable of expressing the polypeptide in accordance with the present invention. The organisms described above may be naturally occurring intact organisms or transformants acquired using the recombinant expression system. According to the method in accordance with the present invention for producing hydroxylated lignans (especially, pinoresinol or piperitol) can be produced efficiently.

In the method of producing hydroxylated lignans according to an embodiment of the present invention, the hydroxylated lignans can be produced using the organism transformed with the polynucleotide encoding the polypeptide in accordance with the present invention or its tissues. Preferably, the organism described above includes the transgenic plants or cells described above, particularly preferably *Escherichia coli, Sesamum indicum, Forsythia intermedia* or *Linum usitatissimum*.

The method of producing hydroxylated lignans according to a preferred embodiment of the present invention comprises the step of introducing the polynucleotide encoding the polypeptide in accordance with the present invention into the organism described above. For the step of introducing the polynucleotide into the organism described above, the various gene transfer methods described above may be used. In this aspect of the embodiment, the organism described above has different compositions between the hydroxylated lignans produced before transformation and the hydroxylated lignans produced after transformation. Specifically, the lignans and hydroxylated lignans obtained from the organism described above provide increased contents of these lignans. Preferably, the method of producing hydroxylated lignans from this aspect of the embodiment further comprises the step of extracting the hydroxylated lignans from the organism described above.

In another embodiment, the method of producing hydroxylated lignans in accordance with the present invention comprises the step of introducing the oligonucleotide in accordance with the present invention as an antisense oligonucleotide into an organism which naturally expresses the polypeptide in accordance with the present invention. For the step of introducing the oligonucleotide into the organism described above, the antisense RNA technique described above may be used. Preferably, the method further comprises the step of using the oligonucleotide described above to identify an organism capable of naturally expressing the polypeptide in accordance with the present invention. The method of producing hydroxylated lignans according to this aspect of the present embodiment further comprises the step of extracting hydroxylated lignans from the organism described above.

In this embodiment, the organism described above has different compositions between the hydroxylated lignans produced before introduction of the oligonucleotide described above and the hydroxylated lignans produced after the introduction. Specifically, the lignans and hydroxylated lignans obtained from the organism described above provide a decreased content of lignans and hydroxylated lignans.

As described above, it may be sufficient that the method of producing hydroxylated lignans in accordance with the present invention comprises at least using the organism capable of expressing the polypeptide in accordance with the present invention.

That is, the object of the present invention is to provide the method of producing hydroxylated lignans based on the organism wherein the composition of hydroxylated lignans is modified by the polypeptide in accordance with the present invention. It should be noted that production methods using animals, plants or various cells as the organism described above are also within the technical scope of the present invention.

(E) Foodstuff and Industrial Product

The present invention provides foodstuff and industrial products manufactured by using the hydroxylated lignans, which are obtained by the method of producing hydroxylated lignans described above. The foodstuff referred to in this section may be any of seeds, fruits, cut panicles, tubers and/or tuberous roots, etc. of the transgenic plants described above, or may be foodstuff (e.g., *Sesamum indicum, Forsythia intermedia* or *Linum usitatissimum*, or their processed foodstuff) manufactured using the hydroxylated lignans extracted from the transgenic plant described above. The foodstuff or industrial products in accordance with the present invention may contain a desired amount of lignans (especially, pinoresinol or piperitol)

For example, the extracts of hydroxylated lignans extracted from the transgenic plant in accordance with the present invention, in which the content of hydroxylated lignans is increased as described above, can be provided as hydroxylated lignan-rich foodstuff. In addition to the extracted lignan glycosides, the seeds, fruits, cut panicles, tubers and/or tuberous roots, etc. of the transgenic plants described above can also be provided as lignan glycoside-rich foodstuff. The target for alteration of the lignan glycoside composition is not particularly limited but, in addition to plants, all organisms including animals, bacteria, yeasts, etc. may be targeted.

Based on the unique physical properties of lignans and hydroxylated lignans, the polypeptide or polynucleotide in accordance with the present invention are also available as raw materials for industrial products (e.g., laboratory reagents, industrial products such as films, biodegradable plastics, functional fibers, lubricants or detergents).

It is obvious to those skilled in the art that the present invention relates to all polypeptides having the lignan-hydroxylating activity and their use. Lignan hydroxylases may be derived from any of plants, animals and microorganisms and can regulate the lignan content, so long as they possess the lignan-hydroxylating activity. The present invention further relates to a plant produced by introducing the polynucleotide encoding lignan hydroxylase, its progeny, or tissues thereof, in which the content of lignan is regulated. The form of plant may be a cut flower. By using the polypeptide for lignan hydroxylation in accordance with the present invention, the production of hydroxylated lignans can be promoted or suppressed. Those skilled in the art can readily understand that the polynucleotide described above is introduced into plants to express the polynucleotide in a constitutive or tissue-specific manner whereby the expression of the target polypeptide can be increased, while it is also possible to repress the expression of the target polypeptide, using the antisense method, the cosuppression method, the RNAi method, etc.

EXAMPLES

The present invention will be described specifically with reference to EXAMPLES below but is not deemed to be limited to these EXAMPLES. Molecular biological techniques were performed according to the methods described in Molecular Cloning (Sambrook, et al., Cold Spring Harbour Laboratory Press, 1989) unless otherwise indicated.

Example 1

Construction of Sesame cDNA Library

Total RNA was extracted from sesame seeds using RNeasy Plant Mini Kit (Qiagen) according to the protocol recommended by the manufacturer. Subsequently, Oligotex-MAG mRNA Purification Kit (TaKaRa) was used to obtain 5 μg of poly A(+) RNA. A cDNA library was prepared from the poly A(+) RNA using ZAP Express cDNA Synthesis Kit and ZAP Express cDNA Gigapack 3 Gold Cloning Kit (Stratagene), according to the protocol recommended by the manufacturer. The library prepared was $1 \times 10^7$ pfu/ml (Reference Document: Ono et al., Proc. Natl. Acad. Sci. USA, 103, 10116-10121, 2006).

Example 2

Production of Hybridization Probes

Total RNA was extracted from Arabidopsis thaliana of the family Brassicaceae using RNeasy Plant Mini Kit (QIAGEN). Subsequently, SuperScript™ First-Strand Synthesis System for RT-PCR (Invitrogen) was used to produce cDNA from 1 μg of the total RNA according to the protocol recommended by the manufacturer. Using as primers At3g13610-Fw (SEQ ID NO: 1) and At3g13610-Rv (SEQ ID NO: 2), 2-oxoglutarate-dependent dioxygenase (hereinafter 2OG-dioxygenase)-like gene At3g13610 from Arabidopsis thaliana was amplified and the resulting amplified fragment was used as a screening probe.

```
SEQ ID NO: 1: At3g13610-Fw:
5'-ATG GCT CCA ACA CTC TTG ACA ACC CAA-3'

SEQ ID NO: 2: At3g13610-Rv:
5'-TCA GAT CTT GGC GTA ATC GAC GGT TTT-3'
```

Using non-radioisotope DIG-Nucleic Acid Detection System (Roche) under the PCR conditions recommended by the manufacturer, DIG label was introduced into the fragment obtained by RT-PCR. Specifically, a PCR solution (50 μl) was composed of 1 μl of each cDNA, 1×Taq buffer (TaKaRa), 0.2 nM dNTPs, 0.4 pmol/μl each of primers (SEQ ID NOS: 1 and 2) and 2.5 U rTaq polymerase. PCR was carried out for 30 cycles of amplification reactions at 94° C. for 5 minutes, then at 94° C. for 1 minute, 53° C. for 1 minute and 72° C. for 2 minutes, followed by maintaining at 72° C. for 2 minutes. This DIG-labeled fragment was used as a hybridization probe in the following experiment.

Example 3

Screening of Sesamum indicum 2OG-Dioxygenase Genes

Using non-radioisotope DIG-Nucleic Acid Detection System (Roche Diagnostics) according to the protocol recommended by the manufacturer, the cDNA library obtained in EXAMPLE 1 was screened with the probe obtained in EXAMPLE 2.

After hybridization at 37° C. for 2 hours in a buffer solution for hybridization (5×SSC, 30% formamide, 50 mM sodium phosphate buffer (pH 7.0), 1% SDS, 2% blocking reagent (Roche), 0.1% lauroylsarcosine and 80 g/ml salmon sperm DNA), the probe obtained in EXAMPLE 2 was added to further continue the incubation overnight. Membrane was washed at 55° C. for 30 minutes in 5×SSC wash solution containing 1% SDS. Approximately $1 \times 10^6$ pfu of plaques were screened to obtain approximately 200 positive clones.

Using a cDNA library synthesis kit according to the protocol recommended by the manufacturer, the 500 clones described above were inserted into pBK-CMV plasmid (Stratagene). A partial DNA sequence of the insert was determined using a primer pair of M13RV and M13M4 (−20). Using the putative amino acid sequence deduced from the determined DNA sequence, database search was performed using Blast x to determine the partial sequences of Sesamum indicum-derived 2OG-dioxygenases (hereinafter SiD). The nucleotide sequences were determined by the primer walking method with a DNA Sequencer Model 3100 (Applied Biosystems) using synthetic oligonucleotide primers. Based on the Clustal-W analysis, seven (7) SiD-like genes (SiD 1 to 7) were finally acquired. The SiD genes except for SiD 4 and SiD 7 did not contain the 5' or 3' region of the putative ORF. Accordingly, the 5' and 3' regions of each SiD gene were amplified by 5' rapid amplification of cDNA ends (hereinafter RACE) according to the protocol recommended by the manufacturer. For RACE, a set of primers (SEQ ID NOS: 3 to 15 and 46) specific for each SiD gene were used. The nucleotide sequence of each amplification product was sequenced by the primer walking method using synthetic oligonucleotide primers to acquire the SiD sequence containing a full-length ORF.

```
SEQ ID NO: 3: GR-SiD1-Fw3:
5'-GGG GAA CGG GCG CAG CTT GCG GGA AGA TT

SEQ ID NO: 4: GR-SiD1-Rv3:
5'-GGC ATC ACC ATC GGT TCC CCC ACC GTG AAA

SEQ ID NO: 5: SiD1-nest-Fw2:
5'-TGA TCT CGT GCT GGG GTT GAA

SEQ ID NO: 6: SiD1-nest-Rv:
5'-TGC TCA TAA TCT CCA TTT GGT

SEQ ID NO: 7: GR-SiD2-Fw:
5'-GGT CGA CAC AAG GAC GGC GGG GCG TTA

SEQ ID NO: 8: GR-SiD2-Rv:
5'-ACG CCC CGC CGT CCT TGT GTC GAC CTA

SEQ ID NO: 9: SiD2-nest-Fw:
5'-ACT GAT GGC GAA TGG ATT CTT

SEQ ID NO: 10: SiD2-nest-Rv2:
5'-TTC CTT CCA GTC CCT GAC ATT

SEQ ID NO: 11: GR-SiD3-Rv:
5'-GGG GTT CGG ACA CTT GGG GTA GTA GA

SEQ ID NO: 12: SiD3-nest-Rv:
5'-CAA GGC GGA TTC TTT GAC CTT

SEQ ID NO: 13: GR-SiD5-Rv:
5'-TGA TCC ACT TCT CGC CCC GCC GGA CTT

SEQ ID NO: 14: SiD5-nest-Rv:
5'-TGA GGG CAT TTT GGG TAA TAG

SEQ ID NO: 15: GR-SiD6-Rv:
5'-TGC GGG TCA GGT GGA TGA GGG GCC ATT

SEQ ID NO: 46: SiD6-nest-Rv:
5'-CAT TAC ACA AGT GAT AGT AT
```

The amino acid sequence and DNA sequence of each SiD gene containing the full-length ORF obtained are shown below (SEQ ID NOS: 16 to 19).

SEQ ID NO: 16: Sid1 protein
MAGVASPPAEVLLSKRVQELVITGEDPSGPYVCRNDDDNGELDATTEN
SPIPVVNIGHFLSGKWSDDESVQELKKLHSALSTWGCFQGIGHGIPSC
FLDEVRRVGREFFEQPMEEKNKYGKTVTEFQGYGADPVPEEGQSLDWS
DRLFLELVPEDQRNYRFWPQNPSSFKGTLEEYSEKMKTVTEIISKSMA
RSLHLEETCFLKQFGERAQLAGRFNYYSPCRRPDLVLGLKPHADGSGY
TVILQDEPGLQVLNHGKWYTVPKNPDALLVLMGDQMEIMSNGVFRSPV
HRVLSNGERDRISVAVFYTPEVGKEIGPEEGLISAEAPRVFKMVKDYA
DIHVGYYQRGMRSLHTVRV SEQ ID NO: 17: Sid1 DNA
ATGGCTGGAGTTGCATCCCCACCCGCTGAAGTATTGCTGTCCAAAAGA
GTCCAAGAATTGGTCATCACCGGTGAGGACCCGTCGGGGCCATACGTG
TGTAGAAACGACGACGACAACGGGGAATTAGACGCGACAACTGAGAAT
TCTCCGATTCCAGTTGTGAACATTGGACACTTCTTGTCGGGAAAATGG
TCCGATGATGAAAGTGTACAAGAGCTGAAGAAACTCCACTCGGCTCTC
TCCACATGGGGATGCTTTCAGGGCATAGGTCATGGGATCCCGAGTTGT
TTCCTGGACGAGGTACGAAGAGTTGGGAGGGAGTTCTTCGAGCAGCCA
ATGGAGGAGAAGAACAAGTATGGGAAAACGGTGACGGAGTTTCAAGGG
TATGGAGCTGATCCCGTCCCGGAAGAAGGGCAGTCGCTCGACTGGTCG
GATCGTCTTTTCCTAGAGTTAGTCCCTGAAGATCAAAGAAATTACAGA
TTCTGGCCTCAGAACCCATCCTCTTTCAAAGGAACACTGGAAGAGTAC
TCGGAGAAGATGAAAACAGTGACTGAGATAATATCCAAATCCATGGCA
AGATCACTTCATCTTGAGGAGACCTGCTTCTTGAAACAGTTCGGGGAA
CGGGCGCAGCTTGCGGGAAGATTCAACTACTATTCGCCTTGCCAGGAGG
CCTGATCTCGTGCTGGGGTTGAAGCCTCACGCCGACGGATCAGGCTAC
ACCGTTATACTGCAGGATGAACCCGGCCTTCAAGTACTCAACCATGGC
AAATGGTATACTGTCCCCAAGAACCCTGATGCCCTTCTAGTCCTCATG
GGGGACCAAATGGAGATTATGAGCAACGGGGTGTTCAGAAGTCCGGTG
CACAGGGTGCTGAGCAATGGGGAGAGGGACAGGATCTCTGTGGCTGTA
TTTTACACGCCGGAGGTGGGAAGGAGATCGGGCCGGAAGAGGGGTTG
ATCAGTGCGGAGGCACCGAGAGTGTTCAAGATGGTGAAAGATTATGCT
GACATTCACGTGGGGTACTATCAGAGGGGAATGAGATCGCTTCATACT
GTCAGAGTTTGATGCTCTATATATATAGGGAAAGTTTAGTCCATCTCG
AGTTTGGTCAGATCTAAATCAATTATATGTCAAGTCAATACATTTGTC
GTGATTAGTGTATAATTTAAAAAATGACTAATCATGTGACAAATGTAT
CACACTTGCTCTATAATTGATTTAGTTCAATGAAAGCTGATATAGATA
AAAATTTTGCATGTANATATGGNGTGTTGTTGGATGCCTTTCCAATGTT
TAAATAACCATATTGCTGCTTGGGATTTCTTTTG SEQ ID NO: 18: Sid2 protein
MGEVDPAFIQALEHRPKPHSVEAQGIPLIDLSPANSPDPDPGSLSALA
AEIGDACEKWGFFQVINHGVPLHVREKIDLVSRKFFALPKEEKKKVSR
DEVNPSGYYDTEHTKNVRDWKEVFDFTVGEPMVMPASHEPDDRELKEV
INQWPENPSEMREVCEEYGAEMQKLGHKLLELIALSLGLARDRFNGFF
KDQTTFIRLNYYAPCPIPDLALGVGRHKDGGALTILAQDDVGGLEVKR
KTDGEWILVKPTPDAYIINVGDIIQVWSNDKYESVEHRVKVNSERERF
SIPFFLNPAHYTMVEPLEELVNKQNPANYNPYNWGKFFSTRKRSNYKK
LDVENIQIHHFKNY*

SEQ ID NO: 19: Sid2 DNA
ATGGGAGAAGTCGACCCTGCATTCATCCAAGCGCTCGAACACAGGCCT
AAACCCCACAGCGTCGAGGCCCAAGGCATCCCGTTAATCGATCTCTCC
CCCGCCAACTCCCCGGACCCGATCCGGGTTCCCTGTCAGCTCTCGCC
GCCGAAATTGGTGATGCGTGCGAGAAATGGGGATTTTTCCAGGTGATC
AACCACGGGGTGCCGTTGCATGTTCGGGAGAAATTGACCTGGTTTCC
AGGAAATTTTTTGCTCTGCCGAAAGAGGAGAAGAAGAAGGTTTCCAGG
AGATGAGGTGACCCGTCGGGGTATTACGACACTGAGCACACTAAGAAT
GTCAGGGACTGGAAGGAAGTGTTTGATTTCACGGTGGGGGAACCGATG
GTGATGCCGGCTTCGCATGAGCCTGATGACAGGGAGCTGAAAGAAGTG
ATCAATCAGTGGCCTGAGAATCCTTCAGAAATGAGGGAAGTGTGTGAA
GAATACGGTGCAGAAATGCAAAAATTGGGACAAGTTGCTGGAACTC
ATAGCCCTGAGCCTAGGCTTGGCGAGAGATCGATTCAATGGGTTTTTC
AAGGATCAAACCACCTTCATTCGGCTGAATTACTATGCGCCATGCCCG
ATCCCTGATCTAGCTCTTGGCGTAGGTCGACACAAGGACGGCGGGGCG
TTAACAATTCTTGCTCAAGACGATGTAGGGGGCTGGAGGTGAAGAGG
AAAACTGATGGCGAATGGATTCTTGTGAAACCTACTCCTGATGCCTAT
ATAATCAATGTTGGTGACATTATACAGGTTTGGAGCAACGATAAGTAC
GAGAGTGTGGAACACAGAGTGAAAGTGAATTCAGAGAGAGAGAGATTT
TCGATTCCCTTCTTCCTCAACCCTGCACATTATACTATGGTAGAACCG
CTGGAGGAGCTGGTGAACAAGCAGAATCCTGCCAACTACAATCCTTAC
AACTGGGGAAAGTTCTTCTCCACCCGAAAACGCAGTAACTACAAGAAG
CTTGATGTGGAGAACATTCAAATACATCACTTCAAGAACTACTGAAGG
TTGCCCTTTTGGGCCTAAGTGTTCACATTCTCAATGATTATGCTTACA
GACTGATGGATTTGGCTCTCTTGACTGTGCATGTATTATGAATAAATA
ATTACTTTAGATATATTATAAAAAAAAAAAAAAAAAAAA

-continued

SEQ ID NO: 20: Sid3 protein
MSELLSEPDNLIDFMLNKGNGVKGLSQINLKQIPDRFIQPPEERLDHI
QIATQESVPVIDVSRWDDPGIAESICEAAAKWGFFQIINHGIPDEVLE
NVKRAAHDFFELPVEERRRYLKENSPTHTVMLKTSFSPLAEKILEWKD
YLMHYCDGQENEHSKFWPPLSRDQVLDYVNWIKPIIRKLLTVLLNGIK
VEQIDKVKESALMGSPVVTLLYYPKCPNPNVAAGAGRHSDVSSITILL
QDDVGGLYVRATEGDQWIHIAPTKGALVVNIGDVLQIMSNDRYKSIEH
RVFVNGSKNRVSVPVFVNPSSDAIIGPLPEVLKAGEKPIYKHVVFSDY
FNYFFSKGHDGKRSLDYAKI*

SEQ ID NO: 21: Sid3 DNA
ATGTCTGAACTACTCTCGGAACCCGACAACCTCATAGATTTTATGCTG
AACAAAGGAAATGGAGTGAAGGGTCTCTCTCAGATAAACCTTAAACAA
ATCCCAGATCGATTCATCCAGCCCCCTGAAGAAAGATTGGACCATATC
CAAATTGCGACCCAAGAATCCGTACCCGTTATCGATGTGTCCAGATGG
GATGACCCGGGAATTGCAGAATCAATCTGCGAGGCAGCAGCCAAGTGG
GGTTTCTTTCAGATCATCAATCATGGAATCCCAGATGAGGTTCTTGAA
AATGTGAAGAGGGCTGCTCATGATTTCTTTGAGTTGCCTGTTGAGGAG
AGGAGGAGGTATTTGAAGGAGAATTCTCCCACTCACACTGTGATGTTG
AAGACTAGCTTTAGTCCTCTTGCTGAGAAGATTTTGGAGTGGAAAGAC
TATCTTATGCACTACTGTGATGGCAAGAAAATGAGCATTCCAAGTTC
TGGCCACCTTTGTCTAGAGATCAAGTTTTGGACTACGTAAACTGGATA
AAGCCCATTATCAGAAAGCTACTGACAGTGTTGCTCAATGGTATTAAG
GTGGAACAAATTGACAAGGTCAAAGAATCCGCCTTGATGGGCTCACCA
GTTGTCACCCTTCTCTACTACCCAAGTGTCCGAACCCCAATGTTGCA
GCTGGAGCTGGCCGTCACTCTGATGTGTCATCAATCACCATCCTCCTA
CAAGACGACGTAGGTGGACTCTACGTACGAGCAACTGAAGGCGACCAG
TGGATCCATATAGCACCAACCAAAGGAGCTCTTGTTGTAAACATCGGA
GATGTGCTGCAGATCATGAGCAACGACAGGTACAAAAGCATCGAGCAT
CGTGTATTTGTGAATGGGAGCAAGAACAGGGTTTCCGTGCCCGTCTTT
GTCAACCCTTCAAGTGACGCCATCATTGGGCCTCTGCCGGAAGTGCTG
AAGGCCGGAGAGAAACCAATCTATAAACATGTTGTCTTCTCGGATTAC
TTCAATTACTTCTTTAGTAAAGGTCATGATGGCAAACGATCGCTGGAT
TATGCGAAAATATGACGTGTTTGTGTTTTGTAGGATAGCTTATCTTCA
CAAGTCTTCTGTCTTCTTGCATAGGCTGTGTCATATACTCACAGAT
TTATCTCCG

SEQ ID NO: 22: Sid4 protein
MEPKLTKLGSSLPVPIVQELAKEKLATVPPRYVRPDQHQHTILSALNS
SFPQIPVIDMQKFSDIYIMDSELQALHNACQEWGFFQLINHGVDSAVM
EKMKIEIQEFFNLPIEEKKKFKHEEGDIQGYGQAFVVSEDQKLDWGDV
FAIVTSPIYLRKPHLIAKLPATFRDATEVYASELKVLAMKILKLMAKA
LDMKAEEMETLFAEGMHSMRMNYYPPCPQPELVTGLCPHSDADGLTIL
LQVNEMDGLQIKKDGVWIPVSPLPNAFTINIGDNLEILTNGAYRSIEH
RATVNKEKERISIATFLGANLDGDMGPSPSLVTPQTPAKFKRIGVTQY
LKELFSRELMGKSYLDLMRI*

SEQ ID NO: 23: Sid4 DNA
ATGGAACCAAAATTAACAAAGCTAGGCAGCTCTCTTCCGGTGCCTATC
GTACAAGAATTGGCCAAGGAGAAATTAGCAACGGTTCCTCCAAGATAC
GTGCGCCCAGATCAACATCAACACACGATTCTCTCTGCTCTTAATTCT
TCCTTCCCTCAAATTCCTGTCATCGATATGCAGAAGTTTTCAGACATC
TATATAATGGATTCTGAGCTTCAGGCCCTACATAATGCATGCCAAGAA
TGGGGTTTCTTTCAGTTGATCAACCATGGGGTGGACTCTGCTGTAATG
GAGAAAATGAAGATAGAAATTCAAGAATTCTTTAATCTCCCAATAGAG
GAGAAGAAGAAATTTAAGCATGAGGAAGGGGACATACAGGGTTATGGG
CAAGCCTTTGTTGTATCAGAAGATCAAAGCTCGACTGGGGAGACGTG
TTTGCCATTGTTACCTCACCAATTTACCTCAGAAAGCCTCACTTAATC
GCCAAGCTTCCTGCTACCTTCAGGGACGCCACAGAAGTGTATGCATCG
GAACTCAAAGTTCTCGCCATGAAGATTCTAAAGCTAATGGCAAAAGCC
TTAGACATGAAAGCTGAAGAAATGGAAACGCTATTCGCAGAAGGGATG
CATTCCATGAGGATGAACTACTATCCTCCGTGTCCCCAGCCCGAGCTC
GTCACGGGCCTCTGCCCTCACTCCGATGCAGATGGGCTCACCATTCTC
CTCCAAGTGAATGAAATGGATGGCCTCCAGATCAAGAAAGATGGAGTC
TGGATTCCCGTTTCTCCACTCCCTAATGCCTTCACCATCAATATTGGA
GATAACTTGGAGATTCTGACAAACGGTGCTTATAGGAGCATTGAGCAT
AGAGCAACTGTCAACAAGGAGAAAGAAAGAATCTCCATTGCCACATTT
CTGGGCGCGAATCTAGATGGTGATATGGGTCCGTCGCCAAGCCTCGTC
ACTCCTCAGACTCCGGCAAAATTCAAGAGGATCGGGGTGACTCAATAT
TTGAAGGAACTATTCTCGCGGGAACTCATGGGGAAATCATATCTAGAC
CTTATGAGGATTAGGGTGTAGTACTGGGGTATGGTAATAACACCAAC
ATGAGTTTGTACCTAATAAGTTATCAACCATTAGATTACAAATAATAC
TATGATCATGTGTAAAAAAAAAAAAAAAAAAAAAAAAAAAAAAAAAAA
AAAAAAA

SEQ ID NO: 24: Sid5 protein
MMSCLQSWPEPVVRVQHLSDSGIRVIPERYVKKLSDRPSFCDSLSGEV
NIPVIDMKGLYSDDASVRKKTAGMISGACREWGFFQVVNHGVRQEVMG
RAREAWREFFKLPLEEKQKYANSPSTYEGYGSRLGVEKGISLDWSDYF
FLNYLPLALRDQNKWPALPLSCREMVGEYCREVVELGGRLMKILSSNL
GLEEEYLQEAFGGEEFGACMRVNYYPKCPQPDLTLGLSPHSDPGGMTL LFPDENVSGLQVRRGEKWITVDPVPNAFIVNIGDQLEVLSNGNYKSVE
HRVIVNSEKERVSIALFYNPRGDMLIKPADELVTEDRPPLYPPTVYDE
YRLYMRTRGPRGKSQVHSLKSLQ*

SEQ ID NO: 25: Sid5 DNA
ATGATGAGCTGCTTGCAGAGCTGGCCCGAACCCGTTGTCAGGGTCCAA
CACCTCTCCGACAGCGGGATTCGGGTAATCCCCGAACGCTACGTGAAG
AAACTCTCAGACAGGCCGAGCTTTTGCGACTCCCTCTCCGGCGAAGTT
AACATTCCAGTCATCGACATGAAGGGGTTGTACTCGGACGACGCCTCA
GTCCGGAAGAAGACGGCCGGGATGATCAGCGGGGCATGCCGCGAGTGG
GGGTTCTTCCAGGTGGTGAACCACGGGGTGAGACAGGAGGTGATGGGG
CGGGCCAGGGAGGCGTGGCGCGAGTTTTTTAAGCTGCCGCTGGAGGAG
AAGCAGAAGTACGCGAATTCGCCGAGCACGTATGAGGGGTACGGCAGC
CGCCTGGGTGTGGAGAAGGGAATATCACTGGATTGGAGTGACTACTTT
TTCCTGAATTACCTTCCTCTCGCACTCAGAGACCAGAATAAGTGGCCT
GCACTTCCTCTTTCATGCAGGGAAATGGTGGGAGAGTACTGTAGAGAA
GTGGTTGAACTTGGTGGAAGATTGATGAAGATTCTGTCGAGCAATCTT
GGGCTGGAAGAAGAGTATCTTCAAGAAGCATTTGGAGGGAGGAGTTT
GGGGCATGCATGAGGGTTAACTATTACCCAAAATGCCCTCAACCGGAC
CTCACACTCGGCCTTTCTCCTCATTCCGACCCGGGTGGGATGACCCTT
CTCTTCCCCGACGAGAACGTATCGGGTCTCCAAGTCCGGCGGGGCGAG
AAGTGGATCACCGTCGACCCAGTCCCCAATGCGTTTATCGTCAATA
GGAGATCAACTTGAGGTGTTAAGCAATGGGAATTACAAGAGTGTGGAG
CATAGGGTGATTGTGAATTCAGAGAAAGAGAGTGTCAATCGCATTG
TTCTACAATCCAAGGGGTGATATGCTGATAAAGCCGGCGGATGAGCTG
GTGACGGAGGACCGCCCACCGCTCTACCCGCCCACCGTTTACGACGAG
TATAGGCTGTACATGAGGACAAGGGGCCCTCGTGGCAAGTCCCAAGTC
CATTCACTTAAATCACTTCAATAACTTAATTAATATTATATTTAAATA
ATAATTTTAGGTAGTATTGTTCCATGAATTGTAGTGTTGTTTGTTAAT
TAATTTCCGCATTTTATGTAATTTGGATTGTACTACACATATATATCA
TGACTACTACTCATCATGGGTTAATTAAAAAAAAAAAAAAAAA

SEQ ID NO: 26: Sid6 protein
MEVQTMKVHAYDRLSELKAFDDSKSGVKGLVDAGVTKIPRFFINDNDM
PGSEPCNFNSEAIFPVIDLSGMHHAANRAGIVSRVKEACEKWGFFQII
NHEMPLRVMDEMIAGVRRFHEQDAEVKKKYYGRDVTKKFQYNSNFDLY
KTRAAMWRDTITCVMAPHPPDPQELPDVCRDIMFEYSKHVMRVGHTVY
ELLSEALGLNPSYLRDIGCIESNFIVGHYSPACPEPELTFGIRSHVDF
GLLTILLQDQIGGLQVLHQNQWVDVSPLPGSLIINVGDFIQLISNDKF
KSVKHRALSKRVGPRISVGVFIKPYYADGDNLRVYGPIKELLTEEEPA
IYRETTYKDYERFYFANCDDGTTKLPYFRLGT*

SEQ ID NO: 27: Sid6 DNA
ATGGAAGTTCAGACAATGAAAGTTCATGCATACGATCGACTAAGTGAA
CTAAAAGCATTCGATGATTCAAAATCAGGCGTGAAGGGACTTGTTGAT
GCTGGTGTTACGAAGATCCCACGTTCTTCATTAATGATAATGATATG
CCTGGATCCGAACCGTGCAACTTCAACTCAGAAGCCATCTTTCCAGTC
ATAGATTTATCAGGCATGCACCATGCTGCAAACCGTGCTGGAATTGTC
AGCAGAGTGAAAGAGGCATGTGAGAAGTGGGGATTCTTTCAGATAATC
AATCATGAGATGCCGCTGCAGTGATGGATGAAATGATTGCAGGGGTT
CGAAGATTTCACGAGCAAGATGCTGAGGTTAAGAAGAAATACTACGGT
CGTGATGTCACGAAAAAGTTTCAGTACAATAGCAATTTCGATCTTTAC
AAAACACGGGCGGCCATGTGGAGGGATACTATCACTTGTGTAATGGCC
CCTCATCCACCTGACCCGCAGGAATTGCCAGATGTATGCAGAGACATC
ATGTTTGAATACTCTAAGCATGTCATGAGAGTGGGGCATACCGTGTAT
GAATTGCTGTCGGAGGCTTTGGGCCTCAATCCCAGCTACCTGAGAGAC
ATTGGCTGTATTGAGTCGAATTTCATCGTGGGCCATTATTCTCCGGCT
TGCCCAGAACCAGAACTGACCTTTGGCATCGAAGCCACGTCGACTTC
GGCTTGCTCACAATACTCTTGCAGGACCAGATTGGCGGTCTCCAGGTG
CTTCACCAGAATCAGTGGGTCGACGTTTCTCCCTTGCCTGGAAGTCTA
ATAATAAATGTTGGGGACTTTATACAGCTGATCAGTAACGACAAATTC
AAAAGCGTGAAACACAGAGCACTATCAAAAAGGGTAGGGCCAAGAATT
TCAGTTGGTGTTTTCATTAAACCCTACTACGCTGATGGAGATAATTTG
CGGGTGTACGGACCTATCAAGGAGCTGTTAACTGAAGAAGAGCCGGCT
ATCTACAGGGAAACAACTTATAAAGACTATGAAAGATTCTACTTCGCC
AATTGTGATGACGGAACCACCAAGCTGCCGTATTTCAGGCTGGGCACC
TGATCAATGGTCCTGCAGTGGCAGCTTGTCAAGTACTGGATAGTTGTG
AACTGACCTTCTTCACCA

SEQ ID NO: 28: Sid7 protein
MAWRSQTEANYDRASELKAFDDTKTGVKGLVDSGITQVPRIFITPRND
SDKNLKPSDSQLKFPIIDLENIDEDPIRFKKVVDEVRDASGTWGFFQV
INHGIPGSVLEEMLDGVRKFYEQDPEERKKWYTRDRKRSVVYNSNFDL
YSAPAANWRDTFFCKMAPHPPSPEELPAVCRDIMFEYTKQVLKLGTSL
FKLLSEALGLDANHLGDMKCADGLALLCHYYPFCPQPELTMGASQHAD
SDFLTVLLNDNVTGLQVLYQNQWFDVPSVPGSLVVNVGDLLQLISNDR
LISSEHRVLANNVRSRVSVACFFRSDIDKSDELYGPIQELLSEDNPPK
YRATTMKEYVNYYNAKGLDGTSALLHFRV*

SEQ ID NO: 29: Sid7 DNA
ATGGCCTGGAGATCTCAGACAGAAGCAAACTACGACAGAGCAAGCGAA
CTAAAAGCTTTTGATGACACCAAAACTGGTGTCAAAGGCTTAGTTGAC
AGTGGTATAACCCAAGTCCCGAGAATCTTCATCACCCCACGAAATGAT
TCAGACAAGAACCTTAAACCTTCCGATTCACAACTCAAATTCCCAATA
ATTGACCTCGAAAACATCGATGAAGATCCAATCAGGTTTAAGAAGGTC
GTGGACGAGGTTCGAGATGCTTCAGGGACATGGGGTTTCTTCCAGGTG
ATCAATCATGGGATTCCGGGTTCTGTTTTGGAGGAGATGCTAGATGGG
GTCCGGAAATTCTATGAACAAGATCCTGAGGAGGAGAAAAGTGGTAC
ACAAGGGATAGAAAAAGAAGTGTTGTTTACAATAGCAACTTTGATTTG
TATAGTGCACCAGCAGCTAATTGGAGGGACACTTTCTTCTGTAAAATG
GCTCCTCATCCTCCAAGCCCTGAGGAGTTGCCCGCTGTGTGCAGAGAT
ATAATGTTTGAGTACACAAAGCAAGTTTTGAAACTGGGAACAAGTTTG
TTTAAATTGTTGTCCGAGGCCCTTGGTCTGGATGCCAACCACCTTGGG
GACATGAAATGTGCTGACGGGCTTGCTCTCCTGTGCCATTACTACCCC
TTCTGCCCTCAGCCGGAGTTAACTATGGGCGCCAGCCAGCACGCGGAC
AGTGACTTCCTGACGGTGCTCCTAAATGACAATGTAACCGGCCTGCAA
GTTCTTTACCAAAACCAGTGGTTTGATGTTCCCTCAGTGCCCGGATCT
CTGGTGGTAAATGTTGGAGATCTTCTACAGCTTATATCAAATGATAGG
TTGATTAGTTCGGAGCATAGAGTACTAGCAAACAACGTTCGTTCAAGG
GTATCAGTCGCATGTTTCTTTAGAAGCGACATAGATAAGTCGGACGAG
CTCTACGGACCAATCCAGGAACTCTTGTCTGAAGATAATCCACCAAAA
TACAGGGCAACCACCATGAAAGAGTATGTGAACTACTACAACGCCAAG
GGGTTGGACGGAACTTCTGCTTTGTTACATTTCCGCGTTTGAATTGAA
ATGATATGATGGGAAGATGTTACTTTCCATATTAATATAATCCGGGAA
AACGGAACATTCGAAATGTAGTATGAAAGAAAAATGTGCGGTCTATTT
CTATTTTATTAGTAAAACCATAACGAATGTTGATTAACTATGATTAAA
ATTAAGCTTTCACTTTAAAAAAAAAAAAAAAA

Example 4

Construction of *Escherichia Coli* Expression Vectors of Sesame 2OG-Dioxygenases (SiD)

Primers having the BamHI or BglII site upstream of the initiator methionine codon (ATG) and having the XhoI site downstream of the termination codon of cDNA in each SiD were designed (SEQ ID NO: 30 through 43), and a fragment containing the ORF of each SiD gene was amplified by PCR.

SEQ ID NO: 30: Bgl2NcoI-SiD1-Fw:
5'-TTT AGA TCT TCC ATG GCT GGA GTT GCA TCC CCA

SEQ ID NO: 31: Sid1-endXhoI-Rv:
5'-TTG ACA TAT AAT TGA TTT AGA TCT

SEQ ID NO: 32: BamNco-SiD2-Fw:
5'-AAA GGA TCC ATG GGA GAA GTC GAC CCT GCA TT

SEQ ID NO: 33: SiD2-KpnXho-Rv:
5'-AAA CTC GAG GTA CCC AAC CTT CAG TAG TTC TTG AAG T

SEQ ID NO: 34: Bgl2-SiD3-Fw:
5'-TTT AGA TCT ATG TCT GAA CTA CTC TCG AAA

SEQ ID NO: 35: SiD3-KpnXho-Rv:
5'-AAA CTC GAG GTA CCA ACA CGT CAT ATT TTC GCA TA

SEQ ID NO: 36: BamNco-SiD4-Fw:
5'-AAA GGA TCC ATG GAA CCA AAA TTA ACA AAG CTA

SEQ ID NO: 37: SiD4-KpnXho-Rv:
5'-AAA CTC GAG GTA CCT ACT ACA CCC TAA ATC CTC ATA A

SEQ ID NO: 38: BamHI-SiD5-Fw:
5'-AAA GGA TCC ATG AGC TGC TTG CAG AGC T

SEQ ID NO: 39: SiD5-KpnXho-Rv:
5'-AAA CTC GAG GTA CCT TAA TTA AGT TAT TGA AGT GAT TT

SEQ ID NO: 40: Bgl2Nco-SiD6-Fw:
5'-AAA GAT CTT CCA TGG AAG TTC AGA CAA TGA AA

-continued

SEQ ID NO: 41: SiD6-KpnXho-Rv:
5'-AAA CTC GAG GTA CCT GAT CAG GTG CCC AGC CTG
AAA TA

SEQ ID NO: 42: BamNco-SiD7-Fw:
5'-AAA GGA TCC ATG GCC TGG AGA TCT CAG ACA GAA

SEQ ID NO: 43: SiD7-KpnXho-Rv:
5'-AAA CTC GAG GTA CCT TCA ATT CAA ACG CGG AAA
TGT AA

A PCR solution (25 µl) was composed of template cDNA from sesame seeds, 0.2 pmol/µl of each primer, 1×KOD Plus buffer (TOYOBO), 0.2 mM dNTPs, 1 mM $MgSO_4$, and 1 U KOD Plus polymerase. PCR was carried out for 30 cycles of amplification reactions at 94° C. for 5 minutes, then at 94° C. for 1 minute, 55° C. for 1 minute and 72° C. for 2 minutes, followed by maintaining at 72° C. for 3 minutes. Each PCR product obtained was inserted into the multicloning site of pCR4 Blunt-TOPO Vector (Invitrogen) according to the protocol recommended by the manufacturer. It was confirmed by sequencing analysis that there was no error in each PCR product inserted.

These plasmids into which the seven (7) SiD genes described above were subcloned were digested with BamHI or BglII and XhoI or KpnI. The resulting 1.1 kb of DNA fragment containing the full-length SiD was inserted into the BamHI and XhoI or KpnI site of pET-30a vector (Novagen) as an *Escherichia coli* expression vector to obtain seven (7) SiD *Escherichia coli* expression vectors.

Example 5

Expression Analysis of SiD Genes in *Sesamum Indicum*

The gene expression profiles of seven (7) SiD genes in a sesame plant were analyzed by RT-PCR. Following the prior publication (Ono et al., Proc. Natl. Acad. Sci. USA, 103, 10116-10121 (2006)), sesame was separated into mature leaves, petals, stems, capsules, seeds (stages 1 to 6) and seedlings (days 1 and 7 after germination induction). From 1 g of the organs separated, RNA was extracted using RNeasy Plant Mini Kit (QIAGEN). Using as a template 1 µg of the RNA thus acquired, reverse transcription was performed to obtain cDNA. SuperScript First-Strand Synthesis System for RT-PCR (GIBCO BRL) was used for the synthesis of cDNA under the conditions recommended by the manufacturer of the system. Using as a template the cDNA obtained at each stage, PCR was performed with the primers (SEQ ID NOS: 30 to 43) specific for the SiD genes described in EXAMPLE 4. Also, for comparison in expression levels between the SiD genes and endogenous genes, Si18S-Fw (SEQ ID NO: 44) and Si18S-Rv primers (SEQ ID NO: 45) were synthesized for the gene amplification, using 18S ribosomal RNA from sesame as the internal standard gene.

SEQ ID NO: 44: Si18S-Fw:
5'-TAT GCT TGT CTC AAA GAT TAA

SEQ ID NO: 45: Si18D-Rv:
5'-AAC ATC TAA GGG CAT CAC AGA

A PCR solution was composed of 1 µl of cDNA, 1×Ex-Taq buffer (TaKaRa), 0.2 nM dNTPs, 0.2 pmol/µl of each primer and 1.25 U Ex-Taq polymerase. PCR was carried out for 30 cycles of amplification reactions at 94° C. for 5 minutes, then at 94° C. for 1 minute, 55° C. for 1 minute and 72° C. for 2 minutes, followed by maintaining at 72° C. for 7 minutes. The resulting product was electrophoresed on 1.0% agarose gel and stained with ethidium bromide to detect the amplified fragment. As a result, it was shown that the seven (7) SiD genes exhibited different expression profiles but were all expressed in sesame seeds wherein lignans were accumulated (FIG. 1).

Example 6

Expression of SiD Recombinant Proteins by *Escherichia coli*

The *Escherichia coli* expression vectors of SiD genes constructed in EXAMPLE 4 were transformed into *Escherichia coli* BL21 (DE3) strain in a conventional manner. These *Escherichia coli* recombinants were preincubated overnight at 37° C. in LB medium containing 20 µg/ml ampicillin in a final concentration. An aliquot of the preincubation mixture was added to M9 medium (10 ml) containing 50 µg/ml ampicillin and 0.5% Casamino acid. The mixture was shake-cultured until $A_{600}$ reached 0.6 to 1.0. Next, IPTG (isopropyl-β-D-thiogalactopyranoside) was added to the culture medium to a final concentration of 0.5 mM, followed by further shake culture at 3000 rpm overnight at 30° C. The culture medium was then centrifuged at 4° C. for 10 minutes to collect the cells. After the cells were suspended in 10 ml of buffer solution (30 mM Tris-HCl (pH 7.5), 30 mM NaCl), the suspension was ultrasonicated to lyse *Escherichia coli*. Next, the lysate was centrifuged at 15,000 rpm at 4° C. for 10 minutes. The supernatant obtained was used as a crude enzyme solution for the following activity assay.

Example 7

Enzyme Analysis of SiD Recombinant Protein

Lignans such as pinoresinol and the like can be produced by extracting from *Sesamum indicum* and purifying the same by, for example, a known method (J. Bioscience, Biotechnology and Biochemistry, 67: 1693 (1993)). The substrate was dissolved in a small quantity of DMSO and then in 70% ethanol. The resulting solution was used as the substrate solution (1 mg/ml). After 5 µl of the substrate solution, 145 µl of the above crude enzyme solution of each SiD expressed in *Escherichia coli*, 10 µl of 0.1 M sodium ascorbate, 10 µl of 2-oxoglutarate (2-OG) and 10 µl of 10 mM $FeSO_4$ were mixed in a reaction tube, the mixture was reacted at 30° C. for an hour.

The enzyme reaction was terminated by adding 100% acetonitrile (150 µl) to the reaction tube. After the reaction tube was vigorously agitated with a vortex mixer, the mixture was centrifuged at 15,000 rpm at 4° C. for 5 minutes. The resulting supernatant was washed through a filter (pore size of 0.45 mm, 4 mm Millex-LH, Millipore) and then analyzed using high performance liquid chromatography (hereinafter HPLC). The conditions for the analysis of lignans and hydroxylated lignans were as follows.

Liquid chromatography (Lc-2010C (Shimadzu Corporation)) was performed using a C-30 column (Nomura Chemical, C30-UG-5, 4.6 mm×150 mm). In the mobile phase, 0.1% TFA was used as eluent A and 0.1% TFA-containing 90% acetonitrile as eluent B. The column was equilibrated with a mixture of 65% eluent A and 35% eluent B (20 minutes), and eluted with a linear concentration gradient (eluent A, 65%: eluent B, 35%→eluent A, 0%:eluent B, 100%) over 20 minutes (flow rate of 0.6 ml/min.) and then with 100% eluent B over 7 minutes. Absorption was monitored at 287 nm to detect the compound contained in a sample. The spectra between 190 nm and 400 nm for each peak of the compound were measured using SPD-10AV (Shimadzu Corporation) to detect a substance having two absorption maxima (230 nm and 280 nm) characteristic of lignans. Under the conditions, standard pinoresinol is detected at about 8.7 minutes, standard piperitol at about 12.8 minutes, standard syringaresinol at about 7.9 minutes and standard secoisolariciresinol at about 6.2 minutes, of retention time (FIG. 2).

As a result of the HPLC analysis of the enzyme reaction solution, the product P1 (retention time of about 6.2 minutes) and the product P2 (retention time of about 4.3 minutes) with the spectra of lignans were obtained only in the reaction solution of Sid6 recombinant protein and pinoresinol (FIG. 2). The product P3 with the spectrum of lignan (retention time of about 9.7 minutes) was newly obtained in the reaction solution of the Sid6 recombinant protein and piperitol (FIG. 2). Furthermore, the product P4 with the spectrum of lignan (retention time of about 5.8 minutes) and the product P5 with the spectrum of lignan (retention time of about 4.2 minutes) were newly obtained in the reaction solution of SiD6 and secoisolariciresinol (FIG. 2). On the other hand, any new product was not observed in the reaction solution with secoisolariciresinol (FIG. 2). Any product was not observed for sesamin, sesaminol or sesamolin but also for naringenin, which is one of flavonoids. These results indicate that SiD6 reacts with a lignan having a furan ring and having at least hydroxy and methoxy groups in the vicinity of the benzene ring (FIG. 2).

The crude extract, 10 μl, from SiD6-expressing *Escherichia coli* was applied to SDS-PAGE and stained with CBB. As a result, a prominent band that was not observed in the crude extract from pET-30a vector-transformed *Escherichia coli* was noted at about 45 kDa (FIG. 3). This size coincided with the sum of an apparent molecular weight of 39.1 kDa for the SiD6, the pET-30a vector-derived His-Tag, the thrombin recognition site, the enterokinase recognition site and the S-Tag. For this reason, the band appeared at 45 kDa was confirmed to be recombinant SiD6 protein. When 2OG was removed from the enzyme reaction solution, any new product was not observed (FIG. 2). It was therefore strongly supported that the product observed in the reaction solution was the lignan produced by SiD6.

As a result of the homology search using Blastx program, SiD6 showed the highest 47% sequence identity with desacetoxyvindoline 4-hydroxylase, which is a hydroxylase for the indole alkaloid from Catharanthus roseus. However, no report has been made of this alkaloid so far in Sesamum indicum. Furthermore, the activity of hydroxylating a lignan with an enzyme belonging to the 2OG-dioxygenase family is new.

Exmple 8

LC-MS Analysis of Products by SiD6

The products P1 and P3 by SiD6 in EXAMPLE 7 were analyzed by the LC-MS analysis for molecular weight.

A column packed with 1 ml of Diaion SEPABEADS HP20 resin (Mitsubishi Chemical) was washed with 10 ml of 50% acetone and then equilibrated with 10 ml of distilled water. Subsequently, 200 ml of the enzyme reaction solution containing each product by SiD6 in EXAMPLE 7 was diluted with distilled water to 1 ml in a measuring cylinder, which was then loaded onto the column. After washing with 5 ml of distilled water, the protein and salts were removed. Thereafter, the lignan was eluted using 2 ml of 80% acetone and the eluate was dried with an evaporator.

A column packed with 1 ml of Diaion HP-20 resin (Mitsubishi Chemical) was washed with 5 ml of 50% acetone and equilibrated with 10 ml of water. The enzyme reaction solution containing the pinoresinol product P1 in EXAMPLE 7 was loaded onto the column. After washing out impurities with 5 ml of water, the reaction product was eluted using 2 ml of 80% acetone. After the eluate was evaporated to dryness using an evaporator, the residue was dissolved in 1% formic acid-containing 50% acetonitrile (100 μl). The solution was provided as a sample for LC-MS analysis. The LC conditions are shown below.

Develosil C30-UG-3 Column (Nomura Chemical Co., Ltd., 3.0 mm×150 mm) was used. In the mobile phase, water containing 10 mM ammonium acetate was used as eluent A and 100% acetonitrile was used as eluent B. Elution was performed with a linear concentration gradient (eluent A, 70%:eluent B, 30%→eluent A, 30%:eluent B, 70%) over 10 minutes, followed by isocratic elution with eluent A, 30%: eluent B, 70% over 5 minutes (flow rate of 0.2 ml/min.).

For detection, data at 230-500 nm were collected by Photodiode Array Detector (SPD-M10A, Shimadzu Corporation) to monitor the chromatogram at A280 nm. TOF-MS Detector (LCMS-IT-TOF, Shimadzu Corporation) was connected after a PDA detector to measure the molecular weight. In both positive and negative modes, MS was measured under the conditions interference at the voltages of 4.5 KV and −3.5 KV, respectively, in a molecular weight range of 100-1000 Da.

Under the conditions, pinoresinol and the pinoresinol reaction product P1 were eluted at 10.1 minutes and 7.9 minutes, respectively. Piperitol and the piperitol product P3 were eluted at 13.3 minutes and 10.9 minutes, respectively. The results of the LC-MS analysis indicate that P1 gave molecular ions with m/z 375.13 [M+H]$^+$ in the positive mode and with m/z 373.13 [M+H]$^-$ in the negative mode, suggesting that a hydroxyl group would be added to piperitol.

The foregoing results demonstrate that the sesame-derived SiD6 gene encodes the lignan hydroxylase having the hydroxylation activity on pinoresinol and piperitol.

Example 9

Purification and NMR Analysis of Products by SiD6

In order to identify the hydroxylated positions of P1 and P2 which are the hydroxylated products of pinoresinol and P3 which is the hydroxylated product of piperitol, each product was purified and analyzed for NMR. In the pinoresinol reaction solution, a column packed with 100 ml of Diaion SEPABEADS HP20 resin (Mitsubishi Chemical) was washed with 200 ml of 50% acetone and then equilibrated with 500 ml of distilled water. Subsequently, 100 ml of the enzyme reaction solution containing the products P1 and P2 by SiD6 in EXAMPLE 7 was loaded onto the column. The column was further washed with 200 ml of distilled water to remove proteins. Finally, P1 and P2 were eluted with 200 ml of 50% acetone and the eluate was concentrated under reduced pressure by an evaporator and then lyophilized. The hydroxylated product P3 of piperitol was purified in the same way. Next, the product was fractionated and purified through a column: Develosil C30-UG-5 (20×250 mm, Nomura Chemical) using eluent A: distilled water and eluent B: 90% acetonitrile under the elution conditions of 20%-70% eluent B (60 mins.) for the hydroxylated products (P1, P2) of pinoresinol and 60-100% eluent B (60 mins.) for the hydroxylated product (P3) of piperitol under the flow rate of 6 ml/min at the detection wavelength of 280 nm. The main peak fraction generated was recovered to prepare the lyophilized specimens. As a result of the NMR analysis (BRUKER, 750 MHz), the specimens were identified as follows.

P1: 9-Hydroxylpinoresinol (fraction with an elution time of 31.0 mins.): NMR: δppm (DMSO-d6); 2.47 (1H, dd), 3.08 (1H, t), 3.62 (1H, ddd), 3.66 (1H, t), 3.76 (6H, s), 4.40 (1H, d), 5.30 (1H, d), 5.45 (1H, s), 6.74 (2H, brs), 6.75 (2H, brs), 6.89 (2H, brs).

P2: 9,9'-Dihydroxylpinoresinol (fraction with an elution time of 22.9 mins.): NMR: δppm (DMSO-d6); 2.77 (2H, d), 3.76 (6H, s), 4.75 (2H, d), 5.39 (2H, d), 6.60 (2H, d), 6.73 (2H, d), 6.85 (2H, dd), 7.13 (2H, d).

In P3, each signal was assigned (FIG. 4). As a result, it was confirmed that P3 was 9-hydroxylpiperitol (FIG. 5). 9-Hydroxylpiperitol is a novel compound. Based on the analysis of sesamin metabolites, this novel lignan is considered to be metabolized in vivo and changed into a catechol type lignan to exhibit its antioxidative effects (Prior Publication: Nakai, M., et al. J. Agric. Food. Chem. 51, 1666-1670. (2003)).

The foregoing results indicate that this enzyme is an enzyme having the hydroxylating activity at position 9 of a furofuran lignan (FIG. 6). From the hydroxylated positions of pinoresinol and piperitol it is inferred that P4 and P5 which are the reaction products with syringaresinol would be hydroxylated as well at position 9 or at positions 9,9'.

The present invention is not deemed to be limited to the particular embodiments described above but various modifications can be made without exceeding the scope of the attached claims. The embodiments appropriately modified in combination with technical means without departing from the scope of the claims also remain within the technical scope of the invention.

INDUSTRIAL APPLICABILITY

As described above, the polypeptide and polynucleotide in accordance with the present invention are useful for hydroxylation of lignans. Also, the transformant or cell, in which the polynucleotide in accordance with the present invention is expressively introduced, is extremely useful in producing hydroxylated lignans or products using the same, in the food sector and a variety of industry sectors. Where the transformant above is a plant, the plant itself can be used as foodstuff and is thus very useful in the agriculture sector, etc.

Further by using the polypeptide and polynucleotide in accordance with the present invention in combination with other enzymes (piperitol and sesamin synthase SiP189) discovered by the present inventors, the production system of particular lignan molecular species can be established so that the production volumes of particular lignan molecular species can be expanded. Accordingly, the present invention is widely available for agriculture, food industry and drug industry as well as industries related thereto.

The invention claimed is:

1. An isolated polypeptide having a lignan-hydroxylating activity, said polypeptide comprising:
   (a) the amino acid sequence of SEQ ID NO: 26; or
   (b) an amino sequence encoded by a nucleic acid having at least 98% identity to SEQ ID NO: 27, wherein said polypeptide has lignin-hydroxylation activity at position 9 of piperitol or pinoresinol.

2. The polypeptide having a lignan-hydroxylating activity according to claim 1, wherein said polypeptide comprises the amino acid sequence of SEQ ID NO: 26.

3. An isolated polynucleotide selected from the group consisting of:
   (a) a polynucleotide comprising the nucleotide sequence of SEQ ID NO: 27;
   (b) a polynucleotide encoding a protein comprising the amino acid sequence of SEQ ID NO: 26; and
   (c) a polynucleotide having at least 98% identity to SEQ ID NO: 27, wherein said polynucleotide encodes a polypeptide having lignin-hydroxylation activity at position 9 of piperitol or pinoresinol.

4. The polynucleotide according to claim 3, wherein said polynucleotide consists of the nucleotide sequence of SEQ ID NO: 27.

5. A vector comprising the polynucleotide according to claim 3.

6. A method for producing a polypeptide, said method comprising: incubating the vector according to claim 5 in a solution for cell-free protein synthesis.

7. A transformant having introduced therein the polynucleotide according to claim 3, wherein said transformant is selected from the group consisting of plant, fungi, yeast and bacteria.

8. A lignan-producing transformant having introduced therein the polynucleotide according to claim 3, wherein the content ratio of a hydroxylated lignan is increased by introducing the polynucleotide according to claim 3.

9. The transformant according to claim 7, which is an organism or a progeny thereof that comprises a vector or chimeric gene, said vector or chimeric gene comprising a polynucleotide selected from the group consisting of:
   (a) a polynucleotide comprising the nucleotide sequence of SEQ ID NO: 27;
   (b) a polynucleotide encoding a protein comprising the amino acid sequence of SEQ ID NO: 26; and
   (c) a polynucleotide having at least 98% identity to SEQ ID NO: 27, wherein said polynucleotide encodes a polypeptide having lignin-hydroxylation activity at position 9 of piperitol or pinoresinol;
   or a tissue derived from said transformant, wherein said tissue comprises said vector or chimeric gene.

10. The transformant according to claim 9, wherein the organism is a plant.

11. The transformant according to claim 10, wherein the plant *Sesamum indicum, Forsythia intermedia* or *Linum usitatissimum*.

12. A method for producing a polypeptide, said method comprising: culturing the transformant according to claim 7, and collecting the polypeptide from said transformant.

13. A method for producing a hydroxylated lignan, said method comprising: culturing the transformant according to claim 7, and collecting the hydroxylated lignan from said transformant.

14. The method for producing a hydroxylated lignan according to claim 13, wherein a substrate for the hydroxylated lignan is piperitol or pinoresinol.

15. A host cell comprising the vector according to claim 5.

16. The host cell according to claim 15, wherein said cell is from *Sesamum indicum, Forsythia intermedia* or *Linum usitatissimum*.

17. A method for producing the polypeptide of claim 1, said method comprising: culturing a host cell comprising a polynucleotide selected from the group consisting of:
   (a) a polynucleotide comprising the nucleotide sequence of SEQ ID NO: 27;
   (b) a polynucleotide encoding a protein comprising the amino acid sequence of SEQ ID NO: 26; and
   (c) a polynucleotide having at least 98% identity to SEQ ID NO: 27, wherein said polynucleotide encodes a polypeptide having lignin-hydroxylation activity at position 9 of piperitol or pinoresinol; and
   collecting the polypeptide from said cell.

18. A method for producing a hydroxylated lignan, said method comprising: culturing the cell according to claim 15, and collecting the hydroxylated lignan from said cell.

19. The method for producing a hydroxylated lignan according to claim 18, wherein a substrate for the hydroxylated lignan is piperitol.

20. The method for producing a hydroxylated lignan according to claim 18, wherein a substrate for the hydroxylated lignan is pinoresinol.

21. A method of increasing the content of a hydroxylated lignan in a lignan-producing organism, said method comprising: introducing the polynucleotide according to claim 3 into a lignan-producing organism.

22. The method according to claim 21, wherein the lignan-producing organism is *Sesamum indicum, Forsythia intermedia* or *Linum usitatissimum*.

23. The method according to claim 21, wherein the lignan is piperitol or pinoresinol.

24. A method of decreasing the content of a hydroxylated lignan in a lignan-producing organism, said method comprising: introducing an oligonucleotide consisting of a fragment of a polynucleotide into the lignan-producing organism, said polynucleotide selected from the group consisting of:
   (a) a polynucleotide comprising the nucleotide sequence of SEQ ID NO: 27;
   (b) a polynucleotide encoding a protein comprising the amino acid sequence of SEQ ID NO: 26;
   (c) a polynucleotide having at least 98% identity to SEQ ID NO: 27; and
   (d) the complementary sequence of any one of (a)-(c);
   wherein said oligonucleotide reduces the expression of an endogenous polynucleotide having lignin-hydroxylation activity at position 9 of piperitol or pinoresinol in said organism comprising any one of (a)-(d).

25. The method according to claim 24, wherein the lignan-producing organism is *Sesamum indicum, Forsythia intermedia* or *Linum usitatissimum*.

26. The method according to claim 24, wherein the lignan is piperitol or pinoresinol.

* * * * *

```
                        SEQUENCE LISTING

<160> NUMBER OF SEQ ID NOS: 47

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      At3g13610-Fw primer

<400> SEQUENCE: 1
atggctccaa cactcttgac aacccaa                                           27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      At3g13610-Rv primer

<400> SEQUENCE: 2
tcagatcttg gcgtaatcga cggtttt                                           27

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      GR-SiD1-Fw3 primer

<400> SEQUENCE: 3
ggggaacggg cgcagcttgc gggaagatt                                         29
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      GR-SiD1-Rv3 primer

<400> SEQUENCE: 4
ggcatcacca tcggttcccc caccgtgaaa                                      30

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      SiD1-nest-Fw2 primer

<400> SEQUENCE: 5
tgatctcgtg ctggggttga a                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      SiD1-nest-Rv primer

<400> SEQUENCE: 6
tgctcataat ctccatttgg t                                               21

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      GR-SiD2-Fw primer

<400> SEQUENCE: 7
ggtcgacaca aggacggcgg ggcgtta                                         27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      GR-SiD2-Rv primer

<400> SEQUENCE: 8
acgccccgcc gtccttgtgt cgaccta                                         27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      SiD2-nest-Fw primer

<400> SEQUENCE: 9
actgatggcg aatggattct t                                               21

```
<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      SiD2-nest -Rv2 primer

<400> SEQUENCE: 10
ttccttccag tccctgacat t                                              21

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      GR-SiD3-Rv primer

<400> SEQUENCE: 11
ggggttcgga cacttggggt agtaga                                         26

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      SiD3-nest-Rv primer

<400> SEQUENCE: 12
caaggcggat tctttgacct t                                              21

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      GR-SiD5-Rv primer

<400> SEQUENCE: 13
tgatccactt ctcgccccgc cggactt                                        27

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      SiD5-nest-Rv primer

<400> SEQUENCE: 14
tgagggcatt ttgggtaata g                                              21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      GR-SiD6-Rv primer

<400> SEQUENCE: 15
tgcgggtcag gtggatgagg ggccatt                                        27
```

```
<210> SEQ ID NO 16
<211> LENGTH: 355
<212> TYPE: PRT
<213> ORGANISM: Sesamum indicum
<220> FEATURE:
<223> OTHER INFORMATION: Sid1 protein

<400> SEQUENCE: 16

Met Ala Gly Val Ala Ser Pro Pro Ala Glu Val Leu Leu Ser Lys Arg
1               5                   10                  15

Val Gln Glu Leu Val Ile Thr Gly Glu Asp Pro Ser Gly Pro Tyr Val
            20                  25                  30

Cys Arg Asn Asp Asp Asn Gly Glu Leu Asp Ala Thr Thr Glu Asn
        35                  40                  45

Ser Pro Ile Pro Val Val Asn Ile Gly His Phe Leu Ser Gly Lys Trp
50                  55                  60

Ser Asp Asp Glu Ser Val Gln Glu Leu Lys Lys Leu His Ser Ala Leu
65                  70                  75                  80

Ser Thr Trp Gly Cys Phe Gln Gly Ile Gly His Gly Ile Pro Ser Cys
                85                  90                  95

Phe Leu Asp Glu Val Arg Arg Val Gly Arg Glu Phe Phe Glu Gln Pro
            100                 105                 110

Met Glu Glu Lys Asn Lys Tyr Gly Lys Thr Val Thr Glu Phe Gln Gly
        115                 120                 125

Tyr Gly Ala Asp Pro Val Pro Glu Glu Gly Gln Ser Leu Asp Trp Ser
    130                 135                 140

Asp Arg Leu Phe Leu Glu Leu Val Pro Glu Asp Gln Arg Asn Tyr Arg
145                 150                 155                 160

Phe Trp Pro Gln Asn Pro Ser Ser Phe Lys Gly Thr Leu Glu Glu Tyr
                165                 170                 175

Ser Glu Lys Met Lys Thr Val Thr Glu Ile Ile Ser Lys Ser Met Ala
            180                 185                 190

Arg Ser Leu His Leu Glu Glu Thr Cys Phe Leu Lys Gln Phe Gly Glu
        195                 200                 205

Arg Ala Gln Leu Ala Gly Arg Phe Asn Tyr Tyr Ser Pro Cys Arg Arg
    210                 215                 220

Pro Asp Leu Val Leu Gly Leu Lys Pro His Ala Asp Gly Ser Gly Tyr
225                 230                 235                 240

Thr Val Ile Leu Gln Asp Glu Pro Gly Leu Gln Val Leu Asn His Gly
                245                 250                 255

Lys Trp Tyr Thr Val Pro Lys Asn Pro Asp Ala Leu Leu Val Leu Met
            260                 265                 270

Gly Asp Gln Met Glu Ile Met Ser Asn Gly Val Phe Arg Ser Pro Val
        275                 280                 285

His Arg Val Leu Ser Asn Gly Glu Arg Asp Arg Ile Ser Val Ala Val
    290                 295                 300

Phe Tyr Thr Pro Glu Val Gly Lys Glu Ile Gly Pro Glu Glu Gly Leu
305                 310                 315                 320

Ile Ser Ala Glu Ala Pro Arg Val Phe Lys Met Val Lys Asp Tyr Ala
                325                 330                 335

Asp Ile His Val Gly Tyr Tyr Gln Arg Gly Met Arg Ser Leu His Thr
            340                 345                 350

Val Arg Val
        355
```

<210> SEQ ID NO 17
<211> LENGTH: 1330
<212> TYPE: DNA
<213> ORGANISM: Sesamum indicum
<220> FEATURE:
<223> OTHER INFORMATION: Sid1 DNA
<220> FEATURE:
<221> NAME/KEY: modified_base
<222> LOCATION: (1264)..(1264)
<223> OTHER INFORMATION: a, c, g, or t
<220> FEATURE:
<221> NAME/KEY: modified_base
<222> LOCATION: (1271)..(1271)
<223> OTHER INFORMATION: a, c, g, or t

<400> SEQUENCE: 17

```
atggctggag ttgcatcccc acccgctgaa gtattgctgt ccaaaagagt ccaagaattg      60
gtcatcaccg gtgaggaccc gtcggggcca tacgtgtgta aaacgacga cgacaacggg     120
gaattagacg cgacaactga gaattctccg attccagttg tgaacattgg acacttcttg     180
tcgggaaaat ggtccgatga tgaaagtgta caagagctga agaaactcca ctcggctctc     240
tccacatggg gatgctttca gggcataggt catgggatcc cgagttgttt cctggacgag     300
gtacgaaagag ttgggaggga gttcttcgag cagccaatgg aggagaagaa caagtatggg     360
aaaacggtga cggagtttca agggtatgga gctgatcccg tcccggaaga agggcagtcg     420
ctcgactggt cggatcgtct tttcctagag ttagtccctg aagatcaaag aaattacaga     480
ttctggcctc agaacccatc ctctttcaaa ggaacactgg aagagtactc ggagaagatg     540
aaaacagtga ctgagataat atccaaatcc atggcaagat cacttcatct tgaggagacc     600
tgcttcttga aacagttcgg ggaacgggcg cagcttgcgg aagattcaa ctactattcg     660
ccttgcagga ggcctgatct cgtgctgggg ttgaagcctc acgccgacgg atcaggctac     720
accgttatac tgcaggatga acccggcctt caagtactca accatggcaa atggtatact     780
gtccccaaga accctgatgc ccttctagtc ctcatggggg accaaatgga gattatgagc     840
aacgggtgt tcagaagtcc ggtgcacagg gtgctgagca atggggagag ggacaggatc     900
tctgtggctg tattttacac gccggaggtg gggaaggaga tcgggccgga agaggggttg     960
atcagtgcgg aggcaccgag agtgttcaag atggtgaaag attatgctga cattcacgtg    1020
gggtactatc agagggggaat gagatcgctt catactgtca gagtttgatg ctctatatat    1080
atagggaaag tttagtccat ctcgagtttg gtcagatcta aatcaattat atgtcaagtc    1140
aatacatttg tcgtgattag tgtataaattt aaaaaatgac taatcatgtg acaaatgtat    1200
cacacttgct ctataattga tttagttcaa tgaaagctga tatagataaa aattttgcat    1260
gtanatatgg ngtgtgttgg atgccttttcc aatgtttaaa taaccatatt gctgcttggg    1320
atttctttg                                                             1330
```

<210> SEQ ID NO 18
<211> LENGTH: 350
<212> TYPE: PRT
<213> ORGANISM: Sesamum indicum
<220> FEATURE:
<223> OTHER INFORMATION: Sid2 protein

<400> SEQUENCE: 18

```
Met Gly Glu Val Asp Pro Ala Phe Ile Gln Ala Leu Glu His Arg Pro
1               5                   10                  15
Lys Pro His Ser Val Glu Ala Gln Gly Ile Pro Leu Ile Asp Leu Ser
            20                  25                  30
```

```
Pro Ala Asn Ser Pro Asp Pro Asp Pro Gly Ser Leu Ser Ala Leu Ala
         35                  40                  45
Ala Glu Ile Gly Asp Ala Cys Glu Lys Trp Gly Phe Phe Gln Val Ile
 50                  55                  60
Asn His Gly Val Pro Leu His Val Arg Glu Lys Ile Asp Leu Val Ser
 65                  70                  75                  80
Arg Lys Phe Phe Ala Leu Pro Lys Glu Lys Lys Val Ser Arg
             85                  90                  95
Asp Glu Val Asn Pro Ser Gly Tyr Tyr Asp Thr Glu His Thr Lys Asn
            100                 105                 110
Val Arg Asp Trp Lys Glu Val Phe Asp Phe Thr Val Gly Glu Pro Met
        115                 120                 125
Val Met Pro Ala Ser His Glu Pro Asp Arg Glu Leu Lys Glu Val
        130                 135                 140
Ile Asn Gln Trp Pro Glu Asn Pro Ser Glu Met Arg Glu Val Cys Glu
145                 150                 155                 160
Glu Tyr Gly Ala Glu Met Gln Lys Leu Gly His Lys Leu Leu Glu Leu
                165                 170                 175
Ile Ala Leu Ser Leu Gly Leu Ala Arg Asp Arg Phe Asn Gly Phe Phe
            180                 185                 190
Lys Asp Gln Thr Thr Phe Ile Arg Leu Asn Tyr Tyr Ala Pro Cys Pro
        195                 200                 205
Ile Pro Asp Leu Ala Leu Gly Val Gly Arg His Lys Asp Gly Gly Ala
210                 215                 220
Leu Thr Ile Leu Ala Gln Asp Asp Val Gly Gly Leu Glu Val Lys Arg
225                 230                 235                 240
Lys Thr Asp Gly Glu Trp Ile Leu Val Lys Pro Thr Pro Asp Ala Tyr
                245                 250                 255
Ile Ile Asn Val Gly Asp Ile Ile Gln Val Trp Ser Asn Asp Lys Tyr
            260                 265                 270
Glu Ser Val Glu His Arg Val Lys Val Asn Ser Glu Arg Glu Arg Phe
        275                 280                 285
Ser Ile Pro Phe Phe Leu Asn Pro Ala His Tyr Thr Met Val Glu Pro
290                 295                 300
Leu Glu Glu Leu Val Asn Lys Gln Asn Pro Ala Asn Tyr Asn Pro Tyr
305                 310                 315                 320
Asn Trp Gly Lys Phe Phe Ser Thr Arg Lys Arg Ser Asn Tyr Lys Lys
                325                 330                 335
Leu Asp Val Glu Asn Ile Gln Ile His His Phe Lys Asn Tyr
            340                 345                 350

<210> SEQ ID NO 19
<211> LENGTH: 1191
<212> TYPE: DNA
<213> ORGANISM: Sesamum indicum
<220> FEATURE:
<223> OTHER INFORMATION: Sid2 DNA

<400> SEQUENCE: 19
atgggagaag tcgaccctgc attcatccaa gcgctcgaac acaggcctaa accccacagc      60
gtcgaggccc aaggcatccc gttaatcgat ctctccccg ccaactcccc ggaccccgat    120
ccgggttccc tgtcagctct cgccgccgaa attggtgatg cgtgcgagaa atggggattt    180
ttccaggtga tcaaccacgg ggtgccgttg catgttcggg agaaaattga cctggtttcc    240
aggaaatttt ttgctctgcc gaaagaggag aagaagaagg tttccaggga tgaggtgaac    300
```

```
ccgtcggggt attacgacac tgagcacact aagaatgtca gggactggaa ggaagtgttt      360
gatttcacgg tgggggaacc gatggtgatg ccggcttcgc atgagcctga tgacagggag      420
ctgaaagaag tgatcaatca gtggcctgag aatccttcag aaatgaggga agtgtgtgaa      480
gaatacggtg cagaaatgca aaaattggga cacaagttgc tggaactcat agccctgagc      540
ctaggcttgg cgagagatcg attcaatggg tttttcaagg atcaaaccac cttcattcgg      600
ctgaattact atgcgccatg cccgatccct gatctagctc ttggcgtagg tcgacacaag      660
gacggcgggg cgttaacaat tcttgctcaa gacgatgtag gggggctgga ggtgaagagg      720
aaaactgatg gcgaatggat tcttgtgaaa cctactcctg atgcctatat aatcaatgtt      780
ggtgacatta tacaggtttg gagcaacgat aagtacgaga gtgtggaaca cagagtgaaa      840
gtgaattcag agagagagag attttcgatt cccttcttcc tcaaccctgc acattatact      900
atggtagaac cgctggagga gctggtgaac aagcagaatc ctgccaacta caatccttac      960
aactggggaa agttcttctc cacccgaaaa cgcagtaact acaagaagct tgatgtggag     1020
aacattcaaa tacatcactt caagaactac tgaaggttgc cctttgggc ctaagtgttc      1080
acattctcaa tgattatgct tacagactga tggatttggc tctcttgact gtgcatgtat     1140
tatgaataaa taattacttt agatatatta taaaaaaaaa aaaaaaaaa a              1191
```

<210> SEQ ID NO 20
<211> LENGTH: 356
<212> TYPE: PRT
<213> ORGANISM: Sesamum indicum
<220> FEATURE:
<223> OTHER INFORMATION: Sid3 protein

<400> SEQUENCE: 20

```
Met Ser Glu Leu Leu Ser Glu Pro Asp Asn Leu Ile Asp Phe Met Leu
1               5                   10                  15

Asn Lys Gly Asn Gly Val Lys Gly Leu Ser Gln Ile Asn Leu Lys Gln
            20                  25                  30

Ile Pro Asp Arg Phe Ile Gln Pro Glu Glu Arg Leu Asp His Ile
        35                  40                  45

Gln Ile Ala Thr Gln Glu Ser Val Pro Val Ile Asp Val Ser Arg Trp
    50                  55                  60

Asp Asp Pro Gly Ile Ala Glu Ser Ile Cys Glu Ala Ala Lys Trp
65                  70                  75                  80

Gly Phe Phe Gln Ile Ile Asn His Gly Ile Pro Asp Glu Val Leu Glu
                85                  90                  95

Asn Val Lys Arg Ala Ala His Asp Phe Phe Glu Leu Pro Val Glu Glu
            100                 105                 110

Arg Arg Arg Tyr Leu Lys Glu Asn Ser Pro Thr His Thr Val Met Leu
        115                 120                 125

Lys Thr Ser Phe Ser Pro Leu Ala Glu Lys Ile Leu Glu Trp Lys Asp
    130                 135                 140

Tyr Leu Met His Tyr Cys Asp Gly Gln Glu Asn Glu His Ser Lys Phe
145                 150                 155                 160

Trp Pro Pro Leu Ser Arg Asp Gln Val Leu Asp Tyr Val Asn Trp Ile
                165                 170                 175

Lys Pro Ile Ile Arg Lys Leu Leu Thr Val Leu Leu Asn Gly Ile Lys
            180                 185                 190

Val Glu Gln Ile Asp Lys Val Lys Glu Ser Ala Leu Met Gly Ser Pro
        195                 200                 205
```

```
Val Val Thr Leu Leu Tyr Tyr Pro Lys Cys Pro Asn Pro Asn Val Ala
            210                 215                 220

Ala Gly Ala Gly Arg His Ser Asp Val Ser Ser Ile Thr Ile Leu Leu
225                 230                 235                 240

Gln Asp Asp Val Gly Gly Leu Tyr Val Arg Ala Thr Glu Gly Asp Gln
                245                 250                 255

Trp Ile His Ile Ala Pro Thr Lys Gly Ala Leu Val Val Asn Ile Gly
            260                 265                 270

Asp Val Leu Gln Ile Met Ser Asn Asp Arg Tyr Lys Ser Ile Glu His
        275                 280                 285

Arg Val Phe Val Asn Gly Ser Lys Asn Arg Val Ser Val Pro Val Phe
    290                 295                 300

Val Asn Pro Ser Ser Asp Ala Ile Ile Gly Pro Leu Pro Glu Val Leu
305                 310                 315                 320

Lys Ala Gly Glu Lys Pro Ile Tyr Lys His Val Val Phe Ser Asp Tyr
                325                 330                 335

Phe Asn Tyr Phe Phe Ser Lys Gly His Asp Gly Lys Arg Ser Leu Asp
            340                 345                 350

Tyr Ala Lys Ile
        355

<210> SEQ ID NO 21
<211> LENGTH: 1161
<212> TYPE: DNA
<213> ORGANISM: Sesamum indicum
<220> FEATURE:
<223> OTHER INFORMATION: Sid3 DNA

<400> SEQUENCE: 21
atgtctgaac tactctcgga acccgacaac ctcatagatt ttatgctgaa caaaggaaat      60
ggagtgaagg gtctctctca gataaacctt aaacaaatcc cagatcgatt catccagccc     120
cctgaagaaa gattggacca tatccaaatt gcgacccaag aatccgtacc cgttatcgat     180
gtgtccagat gggatgaccc gggaattgca gaatcaatct gcgaggcagc agccaagtgg     240
ggtttctttc agatcatcaa tcatggaatc ccagatgagg ttcttgaaaa tgtgaagagg     300
gctgctcatg atttctttga gttgcctgtt gaggagagga ggaggtattt gaaggagaat     360
tctcccactc acactgtgat gttgaagact agctttagtc ctcttgctga aagattttg     420 gagtggaaag actatcttat gcactactgt gatggccaag aaaatgagca ttccaagttc     480
tggccaccct tgtctagaga tcaagttttg gactacgtaa actggataaa gcccattatc     540
agaaagctac tgacagtgtt gctcaatggt attaaggtgg aacaaattga caaggtcaaa     600
gaatccgcct tgatgggctc accagttgtc acccttctct actacccaa gtgtccgaac      660 cccaatgttg cagctggagc tggccgtcac tctgatgtgt catcaatcac catcctccta     720
caagacgacg taggtggact ctacgtacga gcaactgaag cgaccagtg gatccatata      780 gcaccaacca aaggagctct tgttgtaaac atcggagatg tgctgcagat catgagcaac     840
gacaggtaca aaagcatcga gcatcgtgta tttgtgaatg ggagcaagaa cagggttttcc    900 gtgcccgtct tgtcaaccc ttcaagtgac gccatcattg ccctctgcc ggaagtgctg      960 aaggccggag agaaaccaat ctataaacat gttgtcttct cggattactt caattacttc    1020
tttagtaaag gtcatgatgg caaacgatcg ctggattatg cgaaaatatg acgtgtttgt    1080
gttttgtagg atagcttatc ttcacaagtc tttgctgtct tcttgcatag gctgtgtcat    1140
atactcacag atttatctcc g                                              1161
```

```
<210> SEQ ID NO 22
<211> LENGTH: 356
<212> TYPE: PRT
<213> ORGANISM: Sesamum indicum
<220> FEATURE:
<223> OTHER INFORMATION: Sid4 protein

<400> SEQUENCE: 22

Met Glu Pro Lys Leu Thr Lys Leu Gly Ser Ser Leu Pro Val Pro Ile
1               5                   10                  15

Val Gln Glu Leu Ala Lys Glu Lys Leu Ala Thr Val Pro Pro Arg Tyr
                20                  25                  30

Val Arg Pro Asp Gln His Gln His Thr Ile Leu Ser Ala Leu Asn Ser
            35                  40                  45

Ser Phe Pro Gln Ile Pro Val Ile Asp Met Gln Lys Phe Ser Asp Ile
        50                  55                  60

Tyr Ile Met Asp Ser Glu Leu Gln Ala Leu His Asn Ala Cys Gln Glu
65                  70                  75                  80

Trp Gly Phe Phe Gln Leu Ile Asn His Gly Val Asp Ser Ala Val Met
                85                  90                  95

Glu Lys Met Lys Ile Glu Ile Gln Glu Phe Phe Asn Leu Pro Ile Glu
            100                 105                 110

Glu Lys Lys Lys Phe Lys His Glu Glu Gly Asp Ile Gln Gly Tyr Gly
        115                 120                 125

Gln Ala Phe Val Val Ser Glu Asp Gln Lys Leu Asp Trp Gly Asp Val
    130                 135                 140

Phe Ala Ile Val Thr Ser Pro Ile Tyr Leu Arg Lys Pro His Leu Ile
145                 150                 155                 160

Ala Lys Leu Pro Ala Thr Phe Arg Asp Ala Thr Glu Val Tyr Ala Ser
                165                 170                 175

Glu Leu Lys Val Leu Ala Met Lys Ile Leu Lys Leu Met Ala Lys Ala
            180                 185                 190

Leu Asp Met Lys Ala Glu Glu Met Glu Thr Leu Phe Ala Glu Gly Met
        195                 200                 205

His Ser Met Arg Met Asn Tyr Tyr Pro Pro Cys Pro Gln Pro Glu Leu
    210                 215                 220

Val Thr Gly Leu Cys Pro His Ser Asp Ala Asp Gly Leu Thr Ile Leu
225                 230                 235                 240

Leu Gln Val Asn Glu Met Asp Gly Leu Gln Ile Lys Lys Asp Gly Val
                245                 250                 255

Trp Ile Pro Val Ser Pro Leu Pro Asn Ala Phe Thr Ile Asn Ile Gly
            260                 265                 270

Asp Asn Leu Glu Ile Leu Thr Asn Gly Ala Tyr Arg Ser Ile Glu His
        275                 280                 285

Arg Ala Thr Val Asn Lys Glu Lys Glu Arg Ile Ser Ile Ala Thr Phe
    290                 295                 300

Leu Gly Ala Asn Leu Asp Gly Asp Met Gly Pro Ser Pro Ser Leu Val
305                 310                 315                 320

Thr Pro Gln Thr Pro Ala Lys Phe Lys Arg Ile Gly Val Thr Gln Tyr
                325                 330                 335

Leu Lys Glu Leu Phe Ser Arg Glu Leu Met Gly Lys Ser Tyr Leu Asp
            340                 345                 350

Leu Met Arg Ile
        355
```

<210> SEQ ID NO 23
<211> LENGTH: 1208
<212> TYPE: DNA
<213> ORGANISM: Sesamum indicum
<220> FEATURE:
<223> OTHER INFORMATION: Sid4 DNA

<400> SEQUENCE: 23

| | | | | | |
|---|---|---|---|---|---|
| atggaaccaa | aattaacaaa | gctaggcagc | tctcttccgg | tgcctatcgt | acaagaattg | 60 |
| gccaaggaga | aattagcaac | ggttcctcca | agatacgtgc | gcccagatca | acatcaacac | 120 |
| acgattctct | ctgctcttaa | ttcttccttc | cctcaaattc | ctgtcatcga | tatgcagaag | 180 |
| ttttcagaca | tctatataat | ggattctgag | cttcaggccc | tacataatgc | atgccaagaa | 240 |
| tggggtttct | ttcagttgat | caaccatggg | gtggactctg | ctgtaatgga | gaaaatgaag | 300 |
| atagaaattc | aagaattctt | taatctccca | atagaggaga | agaagaaatt | taagcatgag | 360 |
| gaagggaca | tacagggtta | tgggcaagcc | tttgttgtat | cagaagatca | aaagctcgac | 420 |
| tggggagacg | tgtttgccat | tgttacctca | ccaatttacc | tcagaaagcc | tcacttaatc | 480 |
| gccaagcttc | ctgctacctt | cagggacgcc | acagaagtgt | atgcatcgga | actcaaagtt | 540 |
| ctcgccatga | agattctaaa | gctaatggca | aaagccttag | acatgaaagc | tgaagaaatg | 600 |
| gaaacgctat | tcgcagaagg | gatgcattcc | atgaggatga | actactatcc | tccgtgtccc | 660 |
| cagcccgagc | tcgtcacggg | cctctgccct | cactccgatg | cagatgggct | caccattctc | 720 |
| ctccaagtga | atgaaatgga | tggcctccag | atcaagaaag | atggagtctg | gattcccgtt | 780 |
| tctccactcc | ctaatgcctt | caccatcaat | attggagata | acttggagat | tctgacaaac | 840 |
| ggtgcttata | ggagcattga | gcatagagca | actgtcaaca | aggagaaaga | aagaatctcc | 900 |
| attgccacat | ttctgggcgc | gaatctagat | ggtgatatgg | gtccgtcgcc | aagcctcgtc | 960 |
| actcctcaga | ctccggcaaa | attcaagagg | atcggggtga | ctcaatattt | gaaggaacta | 1020 |
| ttctcgcggg | aactcatggg | gaaatcatat | ctagaccta | tgaggattta | gggtgtagta | 1080 |
| ctggggtatg | gtaataacac | caacatgagt | ttgtacctaa | taagttatca | accattagat | 1140 |
| tacaaataat | actatgatca | tgtgtaaaaa | aaaaaaaaa | aaaaaaaaa | aaaaaaaaa | 1200 |
| aaaaaaaa | | | | | | 1208 |

<210> SEQ ID NO 24
<211> LENGTH: 359
<212> TYPE: PRT
<213> ORGANISM: Sesamum indicum
<220> FEATURE:
<223> OTHER INFORMATION: Sid5 protein

<400> SEQUENCE: 24

Met Met Ser Cys Leu Gln Ser Trp Pro Glu Pro Val Val Arg Val Gln
1               5                   10                  15

His Leu Ser Asp Ser Gly Ile Arg Val Ile Pro Glu Arg Tyr Val Lys
            20                  25                  30

Lys Leu Ser Asp Arg Pro Ser Phe Cys Asp Ser Leu Ser Gly Glu Val
        35                  40                  45

Asn Ile Pro Val Ile Asp Met Lys Gly Leu Tyr Ser Asp Asp Ala Ser
    50                  55                  60

Val Arg Lys Lys Thr Ala Gly Met Ile Ser Gly Ala Cys Arg Glu Trp
65                  70                  75                  80

Gly Phe Phe Gln Val Val Asn His Gly Val Arg Gln Glu Val Met Gly
            85                  90                  95

| Arg | Ala | Arg | Glu | Ala | Trp | Arg | Glu | Phe | Phe | Lys | Leu | Pro | Leu | Glu |
|  | 100 |  |  |  |  | 105 |  |  |  |  | 110 |  |  |  |

Lys Gln Lys Tyr Ala Asn Ser Pro Ser Thr Tyr Glu Gly Tyr Gly Ser
            115                 120                 125

Arg Leu Gly Val Glu Lys Gly Ile Ser Leu Asp Trp Ser Asp Tyr Phe
    130                 135                 140

Phe Leu Asn Tyr Leu Pro Leu Ala Leu Arg Asp Gln Asn Lys Trp Pro
145                 150                 155                 160

Ala Leu Pro Leu Ser Cys Arg Glu Met Val Gly Tyr Cys Arg Glu
                165                 170                 175

Val Val Glu Leu Gly Gly Arg Leu Met Lys Ile Leu Ser Asn Leu
        180                 185                 190

Gly Leu Glu Glu Glu Tyr Leu Gln Glu Ala Phe Gly Gly Glu Phe
        195                 200                 205

Gly Ala Cys Met Arg Val Asn Tyr Tyr Pro Lys Cys Pro Gln Pro Asp
    210                 215                 220

Leu Thr Leu Gly Leu Ser Pro His Ser Asp Pro Gly Gly Met Thr Leu
225                 230                 235                 240

Leu Phe Pro Asp Glu Asn Val Ser Gly Leu Gln Val Arg Arg Gly Glu
                245                 250                 255

Lys Trp Ile Thr Val Asp Pro Val Pro Asn Ala Phe Ile Val Asn Ile
            260                 265                 270

Gly Asp Gln Leu Glu Val Leu Ser Asn Gly Asn Tyr Lys Ser Val Glu
        275                 280                 285

His Arg Val Ile Val Asn Ser Glu Lys Glu Arg Val Ser Ile Ala Leu
        290                 295                 300

Phe Tyr Asn Pro Arg Gly Asp Met Leu Ile Lys Pro Ala Asp Glu Leu
305                 310                 315                 320

Val Thr Glu Asp Arg Pro Pro Leu Tyr Pro Pro Thr Val Tyr Asp Glu
                325                 330                 335

Tyr Arg Leu Tyr Met Arg Thr Arg Gly Pro Arg Gly Lys Ser Gln Val
            340                 345                 350

His Ser Leu Lys Ser Leu Gln
        355

<210> SEQ ID NO 25
<211> LENGTH: 1242
<212> TYPE: DNA
<213> ORGANISM: Sesamum indicum
<220> FEATURE:
<223> OTHER INFORMATION: Sid5 DNA

<400> SEQUENCE: 25
atgatgagct gcttgcagag ctggcccgaa cccgttgtca gggtccaaca cctctccgac        60
agcgggattc gggtaatccc cgaacgctac gtgaagaaac tctcagacag gccgagcttt       120
tgcgactccc tctccggcga agttaacatt ccagtcatcg acatgaaggg gttgtactcg       180
gacgacgcct cagtccggaa gaagacggcc gggatgatca gcgggcatg ccgcgagtgg        240 gggttcttcc aggtggtgaa ccacggggtg agacaggagg tgatggggcg ggccaggag        300 gcgtggcgcg agtttttaa gctgccgctg gaggagaagc agaagtacgc gaattcgccg       360
agcacgtatg aggggtacgg cagccgcctg gtgtgtgaga agggaatatc actggattgg      420
agtgactact ttttcctgaa ttaccttcct ctcgcactca gagaccagaa taagtggcct      480
gcacttcctc tttcatgcag ggaaatggtg ggagagtact gtagagaagt ggttgaactt      540
ggtggaagat tgatgaagat tctgtcgagc aatcttgggc tggaagaaga gtatcttcaa      600

-continued

```
gaagcatttg gaggagagga gtttggggca tgcatgaggg ttaactatta cccaaaatgc    660
cctcaaccgg acctcacact cggcctttct cctcattccg acccgggtgg gatgacccct    720
ctcttccccg acgagaacgt atcgggtctc caagtccggc ggggcgagaa gtggatcacc    780
gtcgacccag tccccaatgc gtttatcgtc aatataggag atcaacttga ggtgttaagc    840
aatgggaatt acaagagtgt ggagcatagg gtgattgtga attcagagaa agagagagtg    900
tcaatcgcat tgttctacaa tccaaggggt gatatgctga taaagccggc ggatgagctg    960
gtgacggagg accgccaccg ctctacccg cccaccgttt acgacgagta taggctgtac   1020
atgaggacaa ggggccctcg tgcaagtcc caagtccatt cacttaaatc acttcaataa   1080
cttaattaat attatattta ataataatt ttaggtagta ttgttccatg aattgtagtg   1140
ttgtttgtta attaatttcc gcattttatg taatttggat tgtactacac atatatatca   1200
tgactactac tcatcatggg ttaattaaaa aaaaaaaaaa aa                      1242
```

<210> SEQ ID NO 26
<211> LENGTH: 368
<212> TYPE: PRT
<213> ORGANISM: Sesamum indicum
<220> FEATURE:
<223> OTHER INFORMATION: Sid6 protein

<400> SEQUENCE: 26

```
Met Glu Val Gln Thr Met Lys Val His Ala Tyr Asp Arg Leu Ser Glu
1               5                   10                  15

Leu Lys Ala Phe Asp Asp Ser Lys Ser Gly Val Lys Gly Leu Val Asp
            20                  25                  30

Ala Gly Val Thr Lys Ile Pro Arg Phe Phe Ile Asn Asp Asn Asp Met
        35                  40                  45

Pro Gly Ser Glu Pro Cys Asn Phe Asn Ser Glu Ala Ile Phe Pro Val
    50                  55                  60

Ile Asp Leu Ser Gly Met His His Ala Ala Asn Arg Ala Gly Ile Val
65                  70                  75                  80

Ser Arg Val Lys Glu Ala Cys Glu Lys Trp Gly Phe Phe Gln Ile Ile
                85                  90                  95

Asn His Glu Met Pro Leu Arg Val Met Asp Glu Met Ile Ala Gly Val
            100                 105                 110

Arg Arg Phe His Glu Gln Asp Ala Glu Val Lys Lys Tyr Tyr Gly
        115                 120                 125

Arg Asp Val Thr Lys Lys Phe Gln Tyr Asn Ser Asn Phe Asp Leu Tyr
    130                 135                 140

Lys Thr Arg Ala Ala Met Trp Arg Asp Thr Ile Thr Cys Val Met Ala
145                 150                 155                 160

Pro His Pro Pro Asp Pro Gln Glu Leu Pro Asp Val Cys Arg Asp Ile
                165                 170                 175

Met Phe Glu Tyr Ser Lys His Val Met Arg Val Gly His Thr Val Tyr
            180                 185                 190

Glu Leu Leu Ser Glu Ala Leu Gly Leu Asn Pro Ser Tyr Leu Arg Asp
        195                 200                 205

Ile Gly Cys Ile Glu Ser Asn Phe Ile Val Gly His Tyr Ser Pro Ala
    210                 215                 220

Cys Pro Glu Pro Glu Leu Thr Phe Gly Ile Arg Ser His Val Asp Phe
225                 230                 235                 240

Gly Leu Leu Thr Ile Leu Leu Gln Asp Gln Ile Gly Gly Leu Gln Val
                245                 250                 255
```

| | | | | | | | | | | | |
|---|---|---|---|---|---|---|---|---|---|---|---|
| Leu | His | Gln | Asn | Gln | Trp | Val | Asp | Val | Ser | Pro | Leu | Pro | Gly | Ser | Leu |
| | | 260 | | | | 265 | | | | 270 | |

| Ile | Ile | Asn | Val | Gly | Asp | Phe | Ile | Gln | Leu | Ile | Ser | Asn | Asp | Lys | Phe |
| | | | 275 | | | | 280 | | | | 285 | | | | |

| Lys | Ser | Val | Lys | His | Arg | Ala | Leu | Ser | Lys | Arg | Val | Gly | Pro | Arg | Ile |
| | 290 | | | | | 295 | | | | | 300 | | | | |

| Ser | Val | Gly | Val | Phe | Ile | Lys | Pro | Tyr | Tyr | Ala | Asp | Gly | Asp | Asn | Leu |
| 305 | | | | | 310 | | | | | 315 | | | | | 320 |

| Arg | Val | Tyr | Gly | Pro | Ile | Lys | Glu | Leu | Leu | Thr | Glu | Glu | Pro | Ala |
| | | | | 325 | | | | | 330 | | | | | 335 |

| Ile | Tyr | Arg | Glu | Thr | Thr | Tyr | Lys | Asp | Tyr | Glu | Arg | Phe | Tyr | Phe | Ala |
| | | | 340 | | | | | 345 | | | | | 350 | | |

| Asn | Cys | Asp | Asp | Gly | Thr | Thr | Lys | Leu | Pro | Tyr | Phe | Arg | Leu | Gly | Thr |
| | | | 355 | | | | | 360 | | | | | 365 | | |

<210> SEQ ID NO 27
<211> LENGTH: 1170
<212> TYPE: DNA
<213> ORGANISM: Sesamum indicum
<220> FEATURE:
<223> OTHER INFORMATION: Sid6 DNA

<400> SEQUENCE: 27

```
atggaagttc agacaatgaa agttcatgca tacgatcgac taagtgaact aaaagcattc      60
gatgattcaa aatcaggcgt gaagggactt gttgatgctg gtgttacgaa gatcccacgc     120
ttcttcatta tgataatga tatgcctgga tccgaaccgt gcaacttcaa ctcagaagcc     180
atctttccag tcatagattt atcaggcatg caccatgctg caaaccgtgc tggaattgtc     240
agcagagtga agaggcatg tgagaagtgg ggattctttc agataatcaa tcatgagatg     300
ccgctgcgag tgatggatga aatgattgca ggggttcgaa gatttcacga gcaagatgct     360
gaggttaaga gaaatacta cggtcgtgat gtcacgaaaa agtttcagta caatagcaat     420
ttcgatcttt acaaaacacg ggcggccatg tggagggata ctatcacttg tgtaatggcc     480
cctcatccac ctgacccgca ggaattgcca gatgtatgca gagacatcat gtttgaatac     540
tctaagcatg tcatgagagt ggggcatacc gtgtatgaat gctgtcgga ggctttgggc     600
ctcaatccca gctacctgag agacattggc tgtattgagt cgaatttcat cgtgggccat     660
tattctccgg cttgcccaga accagaactg acctttggca tcagaagcca cgtcgacttc     720
ggcttgctca caatactctt gcaggaccag attggcggtc tccaggtgct tcaccagaat     780
cagtgggtcg acgtttctcc cttgcctgga agtctaataa taaatgttgg ggactttata     840
cagctgatca gtaacgacaa attcaaaagc gtgaaacaca gagcactatc aaaaagggta     900
gggccaagaa tttcagttgg tgttttcatt aaaccctact acgctgatgg agataatttg     960
cgggtgtacg gacctatcaa ggagctgtta actgaagaag agccggctat ctacagggaa    1020
acaacttata aagactatga agattctac ttcgccaatt gtgatgacgg aaccaccaag    1080
ctgccgtatt tcaggctggg cacctgatca atggtcctgc agtggcagct tgtcaagtac    1140
tggatagttg tgaactgacc ttcttcacca                                     1170
```

<210> SEQ ID NO 28
<211> LENGTH: 365
<212> TYPE: PRT
<213> ORGANISM: Sesamum indicum
<220> FEATURE:
<223> OTHER INFORMATION: Sid7 protein

<400> SEQUENCE: 28

```
Met Ala Trp Arg Ser Gln Thr Glu Ala Asn Tyr Asp Arg Ala Ser Glu
1               5                   10                  15
Leu Lys Ala Phe Asp Asp Thr Lys Thr Gly Val Lys Gly Leu Val Asp
            20                  25                  30
Ser Gly Ile Thr Gln Val Pro Arg Ile Phe Ile Thr Pro Arg Asn Asp
        35                  40                  45
Ser Asp Lys Asn Leu Lys Pro Ser Asp Ser Gln Leu Lys Phe Pro Ile
    50                  55                  60
Ile Asp Leu Glu Asn Ile Asp Glu Asp Pro Ile Arg Phe Lys Lys Val
65                  70                  75                  80
Val Asp Glu Val Arg Asp Ala Ser Gly Thr Trp Gly Phe Phe Gln Val
                85                  90                  95
Ile Asn His Gly Ile Pro Gly Ser Val Leu Glu Met Leu Asp Gly
            100                 105                 110
Val Arg Lys Phe Tyr Glu Gln Asp Pro Glu Arg Lys Lys Trp Tyr
        115                 120                 125
Thr Arg Asp Arg Lys Arg Ser Val Val Tyr Asn Ser Asn Phe Asp Leu
130                 135                 140
Tyr Ser Ala Pro Ala Ala Asn Trp Arg Asp Thr Phe Phe Cys Lys Met
145                 150                 155                 160
Ala Pro His Pro Pro Ser Pro Glu Glu Leu Pro Ala Val Cys Arg Asp
                165                 170                 175
Ile Met Phe Glu Tyr Thr Lys Gln Val Leu Lys Leu Gly Thr Ser Leu
            180                 185                 190
Phe Lys Leu Leu Ser Glu Ala Leu Gly Leu Asp Ala Asn His Leu Gly
        195                 200                 205
Asp Met Lys Cys Ala Asp Gly Leu Ala Leu Leu Cys His Tyr Tyr Pro
    210                 215                 220
Phe Cys Pro Gln Pro Glu Leu Thr Met Gly Ala Ser Gln His Ala Asp
225                 230                 235                 240
Ser Asp Phe Leu Thr Val Leu Leu Asn Asp Asn Val Thr Gly Leu Gln
                245                 250                 255
Val Leu Tyr Gln Asn Gln Trp Phe Asp Val Pro Ser Val Pro Gly Ser
            260                 265                 270
Leu Val Val Asn Val Gly Asp Leu Leu Gln Leu Ile Ser Asn Asp Arg
        275                 280                 285
Leu Ile Ser Ser Glu His Arg Val Leu Ala Asn Asn Val Arg Ser Arg
    290                 295                 300
Val Ser Val Ala Cys Phe Phe Arg Ser Asp Ile Asp Lys Ser Asp Glu
305                 310                 315                 320
Leu Tyr Gly Pro Ile Gln Glu Leu Leu Ser Glu Asp Asn Pro Pro Lys
                325                 330                 335
Tyr Arg Ala Thr Thr Met Lys Glu Tyr Val Asn Tyr Tyr Asn Ala Lys
            340                 345                 350
Gly Leu Asp Gly Thr Ser Ala Leu Leu His Phe Arg Val
        355                 360                 365
```

<210> SEQ ID NO 29
<211> LENGTH: 1281
<212> TYPE: DNA
<213> ORGANISM: Sesamum indicum
<220> FEATURE:
<223> OTHER INFORMATION: Sid7 DNA

<400> SEQUENCE: 29

```
atggcctgga gatctcagac agaagcaaac tacgacagag caagcgaact aaaagctttt      60
gatgacacca aaactggtgt caaaggctta gttgacagtg gtataaccca agtcccgaga     120
atcttcatca ccccacgaaa tgattcagac aagaacctta aaccttccga ttcacaactc     180
aaattcccaa taattgacct cgaaaacatc gatgaagatc caatcaggtt aagaaggtc      240
gtggacgagg ttcgagatgc ttcagggaca tggggtttct tccaggtgat caatcatggg     300
attccgggtt ctgttttgga ggagatgcta gatggggtcc ggaaattcta tgaacaagat     360
cctgaggaga ggaaaaagtg gtacacaagg gatagaaaaa gaagtgttgt ttacaatagc     420
aactttgatt tgtatagtgc accagcagct aattggaggg cactttctt  ctgtaaaatg     480
gctcctcatc ctccaagccc tgaggagttg cccgctgtgt gcagagatat aatgtttgag     540
tacacaaagc aagttttgaa actgggaaca gtttgttta  aattgttgtc cgaggccctt     600
ggtctggatg ccaaccacct tggggacatg aaatgtgctg acgggcttgc tctcctgtgc     660
cattactacc ccttctgccc tcagccggag ttaactatgg gcgccagcca gcacgcggac     720
agtgacttcc tgacggtgct cctaaatgac aatgtaaccg gcctgcaagt tctttaccaa     780
aaccagtggt ttgatgttcc ctcagtgccc ggatctctgg tggtaaatgt tggagatctt     840
ctacagctta tatcaaatga taggttgatt agttcggagc atagagtact agcaaacaac     900
gttcgttcaa gggtatcagt cgcatgtttc tttagaagcg acatagataa gtcggacgag     960
ctctacggac caatccagga actcttgtct gaagataatc caccaaaata cagggcaacc    1020
accatgaaag agtatgtgaa ctactacaac gccaaggggt tggacggaac ttctgctttg    1080
ttacatttcc gcgtttgaat tgaaatgata tgatgggaag atgttacttt  ccatattaat    1140
ataatccggg aaaacggaac attcgaaatg tagtatgaaa gaaaaatgtg cggtctattt    1200
ctattttatt agtaaaacca taacgaatgt tgattaacta tgattaaaat taagctttca    1260
ctttaaaaaa aaaaaaaaaa a                                              1281
```

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      Bgl2NcoI-SiD1-Fw primer

<400> SEQUENCE: 30

```
tttagatctt ccatggctgg agttgcatcc cca                                    33
```

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      Sid1-endXhoI-Rv primer

<400> SEQUENCE: 31

```
ttgacatata attgatttag atct                                              24
```

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      BamNco-SiD2-Fw primer

<400> SEQUENCE: 32
aaaggatcca tgggagaagt cgaccctgca tt                                32

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      SiD2-KpnXho- Rv primer

<400> SEQUENCE: 33
aaactcgagg tacccaacct tcagtagttc ttgaagt                           37

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      Bgl2-SiD3-Fw primer

<400> SEQUENCE: 34
tttagatcta tgtctgaact actctcggaa                                   30

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      SiD3-KpnXho-Rv primer

<400> SEQUENCE: 35
aaactcgagg taccaacacg tcatattttc gcata                             35

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      BamNco-SiD4-Fw primer

<400> SEQUENCE: 36
aaaggatcca tggaaccaaa attaacaaag cta                               33

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      SiD4-KpnXho-Rv primer

<400> SEQUENCE: 37
aaactcgagg tacctactac accctaaatc ctcataa                           37

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      BamHI-SiD5-Fw primer

```
<400> SEQUENCE: 38
aaaggatcca tgagctgctt gcagagct                                    28

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      SiD5-KpnXho-Rv primer

<400> SEQUENCE: 39
aaactcgagg taccttaatt aagttattga agtgattt                         38

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      Bgl2Nco-SiD6-Fw primer

<400> SEQUENCE: 40
aaagatcttc catggaagtt cagacaatga aa                               32

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
      SiD6-KpnXho-Rv primer

<400> SEQUENCE: 41
aaactcgagg tacctgatca ggtgcccagc ctgaaata                         38

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      BamNco-SiD7-Fw primer

<400> SEQUENCE: 42
aaaggatcca tggcctggag atctcagaca gaa                              33

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      SiD7-KpnXho-Rv primer

<400> SEQUENCE: 43
aaactcgagg taccttcaat tcaaacgcgg aaatgtaa                         38

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      Si18S-Fw primer
```

```
<400> SEQUENCE: 44
tatgcttgtc tcaaagatta a                                             21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      Si18D-Rv primer

<400> SEQUENCE: 45
aacatctaag ggcatcacag a                                             21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      SiD6-nest-Rv primer

<400> SEQUENCE: 46
cattacacaa gtgatagtat                                               20

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47

His His His His His His
1               5
```